United States Patent
Shi et al.

(10) Patent No.: US 11,142,545 B2
(45) Date of Patent: Oct. 12, 2021

(54) SYNTHESIS OF THIOLATED OLIGONUCLEOTIDES WITHOUT A CAPPING STEP

(71) Applicant: BIOGEN MA INC., Cambridge, MA (US)

(72) Inventors: Xianglin Shi, Cambridge, MA (US); Jimin Yang, Cambridge, MA (US); William F. Kiesman, Cambridge, MA (US); Yannick Fillon, Cambridge, MA (US)

(73) Assignee: BIOGEN MA INC., Cambridge, MA (US)

( * ) Notice: Subject to any disclaimer, the term of this patent is extended or adjusted under 35 U.S.C. 154(b) by 0 days.

(21) Appl. No.: 16/312,819

(22) PCT Filed: Jun. 22, 2017

(86) PCT No.: PCT/US2017/038643
§ 371 (c)(1),
(2) Date: Dec. 21, 2018

(87) PCT Pub. No.: WO2017/223258
PCT Pub. Date: Dec. 28, 2017

(65) Prior Publication Data
US 2019/0161513 A1    May 30, 2019

Related U.S. Application Data

(60) Provisional application No. 62/354,433, filed on Jun. 24, 2016.

(51) Int. Cl.
| | |
|---|---|
| *C07H 21/04* | (2006.01) |
| *C07H 1/00* | (2006.01) |
| *C07H 21/02* | (2006.01) |
| *C07H 21/00* | (2006.01) |

(52) U.S. Cl.
CPC .............. *C07H 21/04* (2013.01); *C07H 1/00* (2013.01); *C07H 21/00* (2013.01); *C07H 21/02* (2013.01)

(58) Field of Classification Search
CPC .......... C07H 1/00; C07H 21/04; C07H 21/02; C07H 21/00
See application file for complete search history.

(56) References Cited

U.S. PATENT DOCUMENTS

| | | | | |
|---|---|---|---|---|
| 6,087,491 A | * | 7/2000 | Tang | C07H 21/00 536/25.34 |
| 6,124,450 A | * | 9/2000 | Ravikumar | C07F 9/146 536/25.3 |
| 6,310,198 B1 | * | 10/2001 | Tang | C07H 21/00 435/6.1 |
| 6,809,195 B1 | | 10/2004 | Sanghvi et al. | |
| 8,304,532 B2 | * | 11/2012 | Adamo | C07H 21/00 536/25.34 |
| 8,642,755 B2 | * | 2/2014 | Sierzchala | C07H 21/02 536/25.33 |
| 9,725,716 B2 | * | 8/2017 | Burghes | A61K 49/0438 |
| 9,758,546 B2 | * | 9/2017 | Chreng | C07H 21/00 |
| 10,392,419 B2 | * | 8/2019 | Oost | A61K 39/39 |
| 10,449,211 B2 | * | 10/2019 | Katibah | C07H 19/213 |
| 2010/0331533 A1 | | 12/2010 | Sierzchala et al. | |

OTHER PUBLICATIONS

Cheruvallath et al., Synthesis of Antisense Oligonucleotides:? Replacement of 3H-1,2-Benzodithiol-3-one 1,1-Dioxide (Beaucage Reagent) with Phenylacetyl Disulfide (PADS) As Efficient Sulfurization Reagent:? From Bench to Bulk Manufacture of Active Pharmaceutical Ingredient. Org Proc Res Dev. 2000;4(3)199-204.

Lemaître et al., Sulfurizing Reagent li and Its Use In Synthesizing Oligonucleotide Phosphorothioates. The Glen Report. Dec. 2006;18(1):6 pages.

Tang et al., Large-Scale Synthesis of Oligonucleotide Phosphorothioates Using 3-Amino-1,2,4-dithiazole-5-thione as an Efficient Sulfur-Transfer Reagent. Org Proc Res Dev. 2000;4(3):194-198.

International Search Report and Written Opinion for Application No. PCT/US2017/038643, dated Sep. 13, 2017, 12 pages.

* cited by examiner

*Primary Examiner* — Lawrence E Crane
(74) *Attorney, Agent, or Firm* — McCarter & English, LLP; Steven G. Davis; Xin Zhang

(57) ABSTRACT

The invention herein describes a solid-phase synthetic method for preparing thiolated oligonucleotides without needing a capping step. The methods of the invention comprises repetition of a three-reaction per cycle, namely detritylation, coupling and sulfurization, without a capping step. In some embodiments, the synthetic methods of the present invention can be used for preparing an anti-sense oligonucleotide.

21 Claims, 9 Drawing Sheets

Specification includes a Sequence Listing.

SEQUENCE LISTING

<160> NUMBER OF SEQ ID NOS: 8

<210> SEQ ID NO 1
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1
tcactttcat aatgctgg                                                 18

<210> SEQ ID NO 2
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 2
caggatacat ttctacagct                                               20

<210> SEQ ID NO 3
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 3
cgactatacg cgcaatatgg                                               20

<210> SEQ ID NO 4
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 4
cgacuatacg cgcaauaugg                                               20

<210> SEQ ID NO 5
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

```
<220> FEATURE:
<221> NAME/KEY: source
<223> OTHER INFORMATION: /note="Description of Combined DNA/RNA
      Molecule: Synthetic oligonucleotide"

<400> SEQUENCE: 5
cgactatacg cgcaatatgg                                              20

<210> SEQ ID NO 6
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 6
cgacuatacg cgcaauaugg                                              20

<210> SEQ ID NO 7
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 7
cgacuatacg cgcaauaugg                                              20

<210> SEQ ID NO 8
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 8
gcccctagcg cgcgacuc                                                18
```

SYNTHESIS OF THIOLATED OLIGONUCLEOTIDES WITHOUT A CAPPING STEP

RELATED APPLICATIONS

This application is a 35 U.S.C. § 371 national stage filing of International Application No. PCT/US2017/038643, filed on Jun. 22, 2017, which claims the benefit of the filing date under 35 U.S.C. § 119(e), of U.S. Provisional Patent Application No. 62/354,433, filed on Jun. 24, 2016. The entire content of each of the foregoing applications is hereby incorporated by reference.

SEQUENCE LISTING

The instant application contains a Sequence Listing which has been submitted electronically in ASCII format and is hereby incorporated by reference in its entirety. Said ASCII copy, created on Jun. 20, 2017, is named 123429-00220_SL.txt and is 3,101 bytes in size.

BACKGROUND OF THE INVENTION

Oligonucleotides are short DNA or RNA oligomers that can be chemically synthesized for research and medical purposes. Oligonucleotides are typically prepared by a stepwise addition of nucleotide residues to produce a specific sequence. Current solid-phase synthesis manufacturing process of thiolated oligonucleotides uses repetition of four-reactions per cycle, namely deprotection (e.g., detritylation), coupling, sulfurization, and capping. The capping step was designed to block any unreacted 5'-hydroxyl groups that failed to couple with the phosphoramidite in each cycle, so the failure sequence does not participate further in the coupling reactions in the subsequent cycles to generate impurities missing the nucleoside of the failed coupling. The capping step is done typically using acetic anhydride with base catalysts, such as pyridine or N-methyl morpholine.

As each of the four steps need to be completed to add each nucleotide to the growing oligomer, reducing the number of steps would reduce the amount of time required for each nucleotide addition, as well reduce the amount of reagents required to complete the oligonucleotide synthesis. Therefore, new synthetic methods for preparing oligonucleotides are needed.

SUMMARY OF THE INVENTION

The invention herein describes a solid-phase synthesis manufacturing process for fully or partially thiolated oligonucleotides using repetition of a-three-reactions per cycle, namely detritylation, coupling, and sulfurization, rather than conventional four-reactions per cycle.

Typically, nucleotides are added to a growing oligomer chain by coupling the free 5'-hydroxyl of the last nucleotide of the oligomer attached to the solid support with the appropriate phosphoramidite. Inefficiencies in the coupling reaction would leave some of the 5'-hydroxyl groups free to react in subsequent coupling reactions, resulting in a complicated mixture of oligomers missing a single, but random, nucleotide. Accordingly, to prevent the unreacted 5'-hydroxyl from later reacting, the 5'-hydroxyl is capped via the use of a capping reagent such as acetic anhydride prior to or after the sulfurization step.

Surprisingly, the present inventors developed a process that eliminates the capping step prior to or following the sulfurization step. In particular, rather than capping the unreacted 5'-hydroxyl groups with a reagent that needs to be newly introduced to the process, for example, acetic anhydride, the present inventors have surprisingly discovered that the byproducts generated during the sulfurization step can be used to cap the unreacted 5'-hydroxy groups. These byproducts or in certain cases, the sulfurization agent itself, for example PADS, may be recirculated across the solid support to cap the 5'-hydroxy groups that failed to couple with the phosphoramidite. The unreacted 5' hydroxyl groups react with the sulfurization byproducts, without the need of a separate capping step, and are no longer available to couple in the subsequent cycles.

For a fully thiolated oligonucleotide (i.e., an oligonucleotide including only phosphothiolate (—P=S) bonds), no capping step is needed at all and the process includes only 3 reactions per cycle (deprotection, coupling, and sulfurization).

The process described herein can be also used to prepare partially thiolated oligonucleotides, which include both phosphothiolate (—P=S) and phosphodiester (—P=O) bonds. Partially thiolated oligonucleotides are conventionally prepared by the 4-reaction step cycle, with the third step in the cycle being either oxidation or sulfurization depending on whether a —P=O or a —P=S bond is desired. Use of the process described herein can be used to eliminate the capping step following the sulfurization step. However, because the byproducts of the oxidation step do not cap the unreacted 5'-hydroxy, residual amounts of unreacted 5'-hydroxyl groups may remain following the oxidation step. However, for partially thiolated oligonucleotides including a small number of —P=O bonds, for example, 4 or less, the process described here in can be used even without a capping step following the oxidation step. For partially thiolated oligonucleotides including a greater number of —P=O bonds, for example, 5 or more, the process described herein can be used but a conventional capping step, for example, with acetic anhydride, may be used following each oxidation step. However, a capping step is still not needed following the sulfurization step regardless of how many —P=O bonds are present.

DETAILED DESCRIPTION

Figure 1:
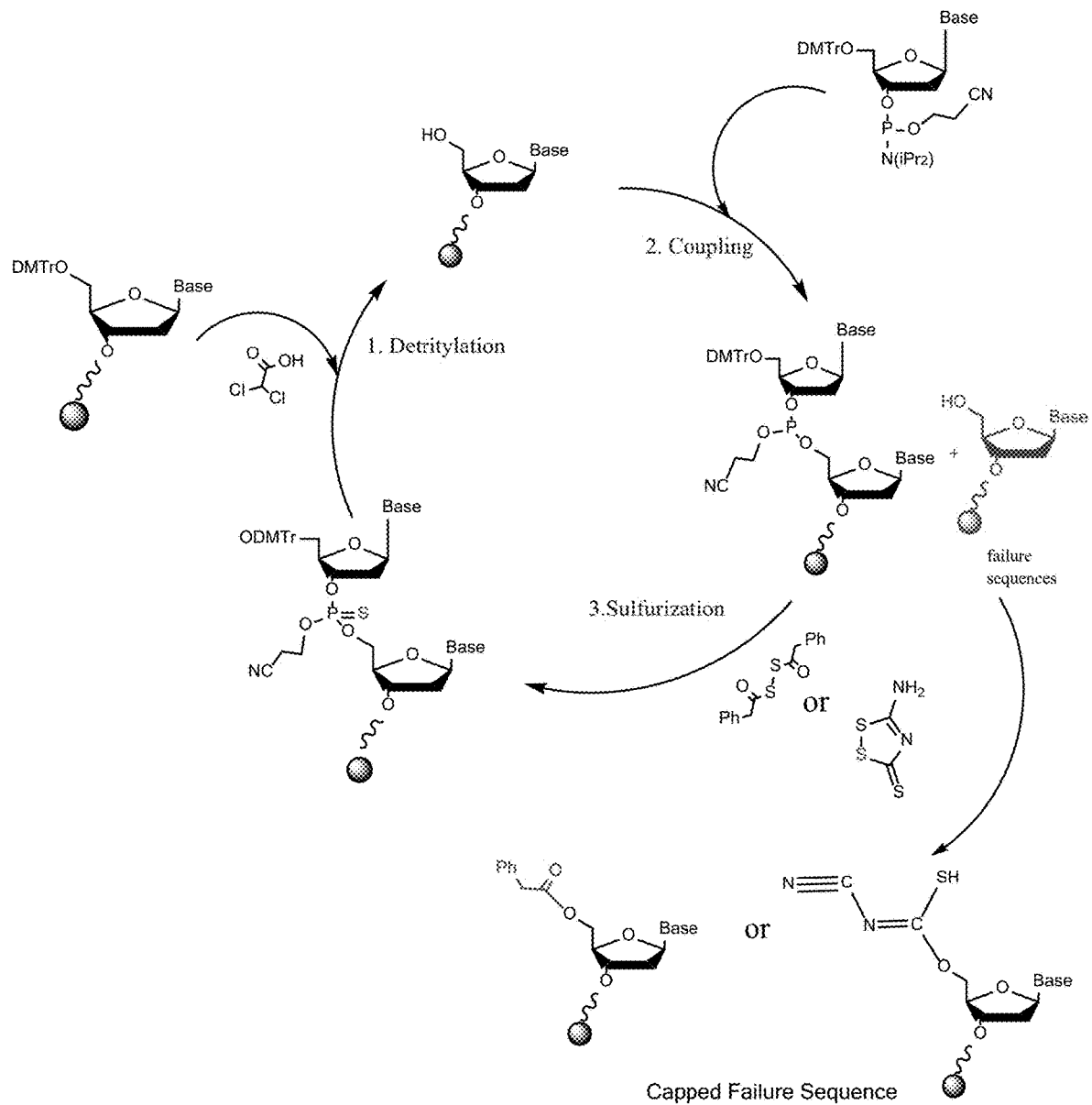
FIG. 1 is a diagram of the 3-step oligonucleotide synthetic method.
Figure 2:
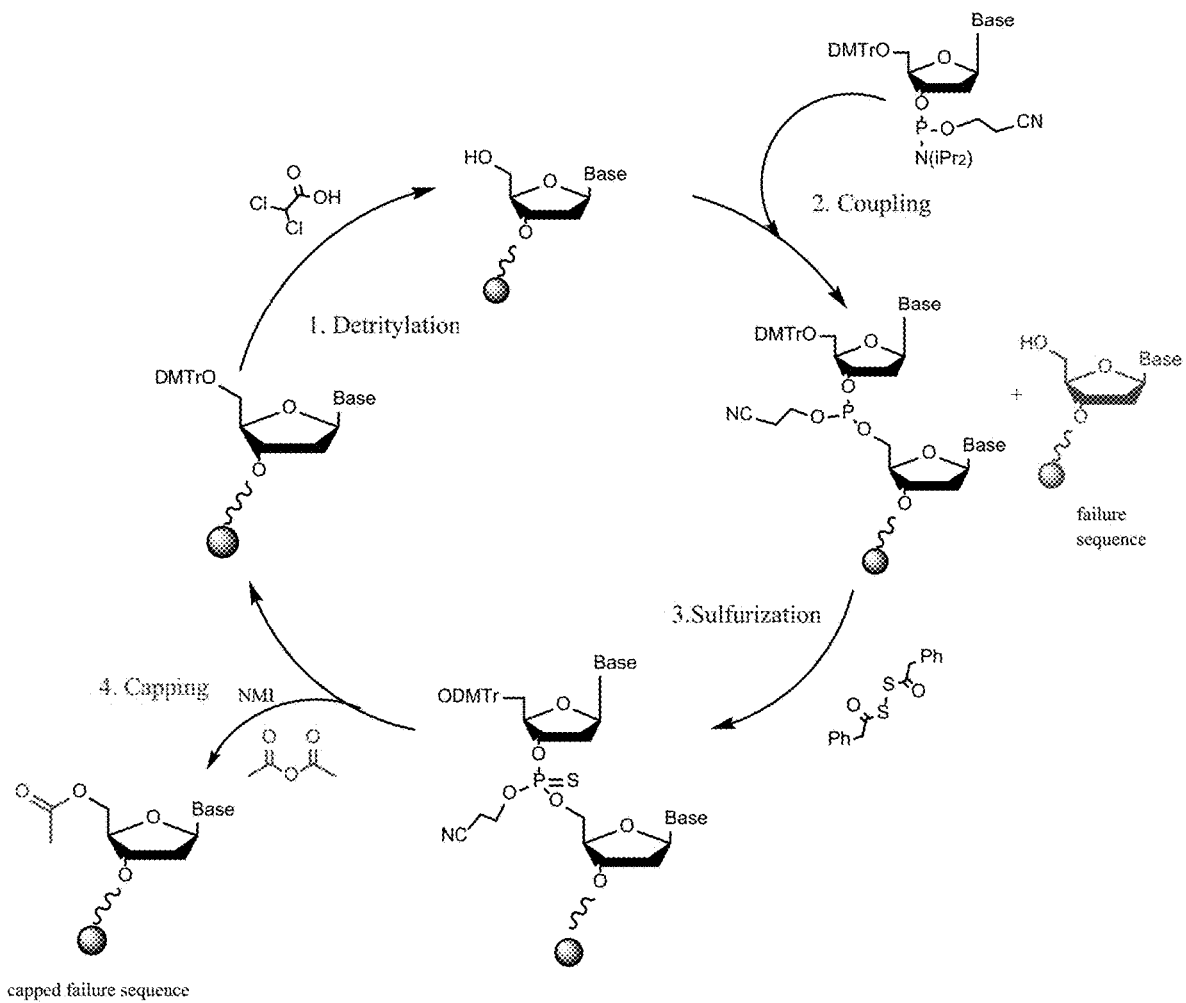
FIG. 2 is a diagram of the conventional 4-step oligonucleotide synthetic method. It is noted that the sulfurization step may be performed before or after the capping step in the conventional 4-reactions per cycle process.

A first embodiment of the invention is a process for preparing an oligonucleotide comprising a) reacting the compound of Formula (I):

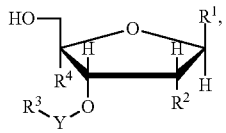

(I)

with the compound of Formula (II):

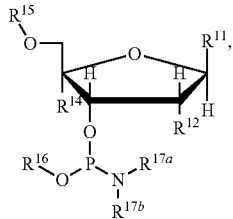

(II)

to form a compound of Formula (III):

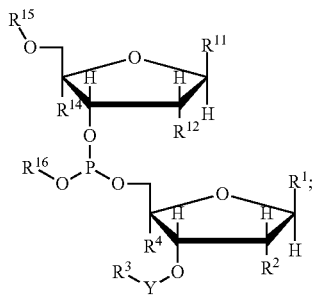

(III)

and b) sulfurizing the compound of Formula (III) with a sulfurization agent to form a compound of Formula (IV):

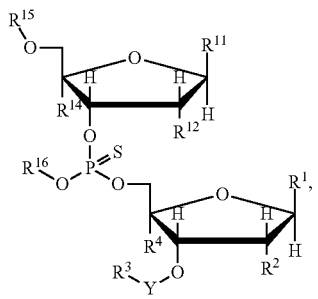

(IV)

and from unreacted compound of Formula (I) forms a compound of Formula (V):

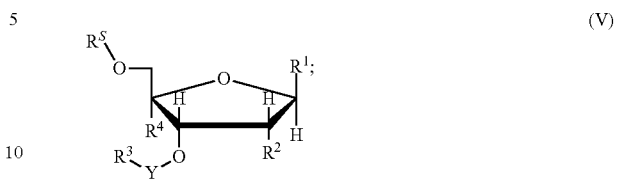

(V)

wherein

Each $R^1$ and $R^{11}$ are independently a nucleobase, wherein the $NH_2$ of the nucleobase, if present, is protected by an amine protecting group;

Each $R^2$ and $R^{12}$ are independently selected from the group consisting of H, halo, and $C_{1-6}$alkoxy optionally substituted with $C_{1-6}$alkoxy;

$R^3$ is a solid support, optionally comprising a linker;

Y is absent, a nucleotide, or an oligonucleotide comprising 2 or more nucleotides;

Each $R^4$ is independently H or forms a ring with the alkoxy group of $R^2$;

Each $R^{14}$ is independently H or forms a ring with the alkoxy group of $R^{12}$;

$R^{15}$ is a hydroxy protecting group;

$R^{16}$ is $C_{1-6}$alkyl optionally substituted with —CN;

$R^{17a}$ and $R^{17b}$ are independently $C_{1-6}$alkyl;

$R^S$ is a hydroxy protecting group formed from a byproduct of the sulfurization agent;

wherein the sulfurization agent is reacted for a sufficient amount of time to substantially completely convert unreacted compound of Formula (I) to the compound of Formula (V) and to convert the compound of Formula (III) to Formula (IV);

wherein a sufficient amount of sulfurization agent is added to substantially completely convert unreacted compound of Formula (I) to Formula (V) and to convert the compound of Formula (III) to Formula (IV); and wherein the compounds of Formulas (I), (II), (III), (IV), and (V) are optionally in the form of a pharmaceutically acceptable salt.

As used herein, "a sufficient amount of time" could be determined by one of skill in the art based upon the reaction conditions. For example, the times provided in the thirteenth embodiment, namely 0 to 30 minutes, for example, 0, 5, 10, 15, 20, 25, or 30 minutes, would be "a sufficient amount of time".

As used herein, "to substantially completely convert" could be determined by one of skill in the art based upon the reaction conditions. In particular, substantially completely convert means to convert 50%, 60%, 65%, 70%, 75%, 80%, 85%, 90%, 95% or 100% of the unreacted compound of Formula (I) to Formula (V) or Formula (III) to Formula (IV).

In some aspects of the first embodiment, the process does not include an additional capping step following step b. Specifically, any unreacted compound of Formula (I), (VI), or (IX) is capped by the byproducts of the sulfurization step b without the require add any other reagent to cap any unreacted compound of Formula (I), (VI), or (IX).

In a particular aspect of the first embodiment, $R^{11}$ is selected from the group consisting of cytosine, guanine, adenine, thymine (or 5-methyl uracil), uracil, hypoxanthine, xanthine, 7-methylguanine, 5,6-dihydrouracil, 5-methylcytosine, and 5-hydroxymethylcytosine, wherein the NH₂ group of the nucleobase, if present, is protected by PhCO—, CH₃CO—, iPrCO—, Me₂N—CH=, or Me₂N—CMe=.

$R^{12}$ is selected from the group consisting of H, halo, $C_{1-4}$alkoxy, and $C_{1-4}$alkoxy$C_{1-4}$alkoxy;

Each $R^{14}$ is independently H or forms a 5- or 6-membered ring with the alkoxy group of $R^{12}$;

$R^{15}$ is a hydroxy protecting group selected from 4,4'-dimethoxytrityl, [bis-(4-methoxyphenyl)phenylmethyl] (DMT) or trityl (triphenylmethyl, Tr).

$R^{16}$ is $C_{1-4}$alkyl substituted with —CN; and $R^{17a}$ and $R^{17b}$ are independently $C_{1-4}$alkyl.

In a particular embodiment,

In a specific aspect of the first embodiment, Formula (II) is selected from any one of the following structural formula:

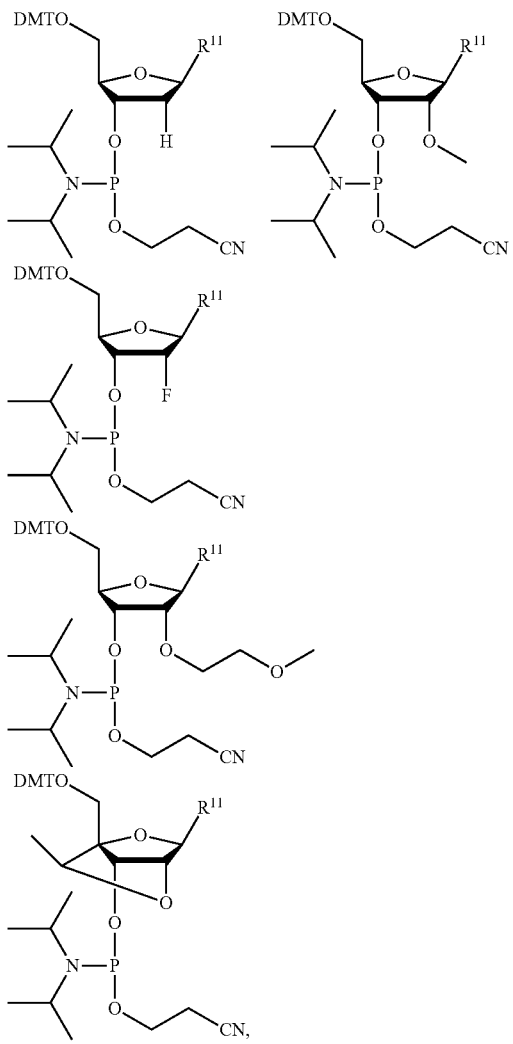

wherein DMTO is the 4,4'-dimethoxytrityl protected 5'-hydroxy and $R^{11}$ is as defined for the first embodiment.

A second embodiment of the invention is a process as described for the first embodiment or any aspect thereof, further comprising the step of c) deprotecting the compound of Formula (IV) to form the compound of Formula (VI):

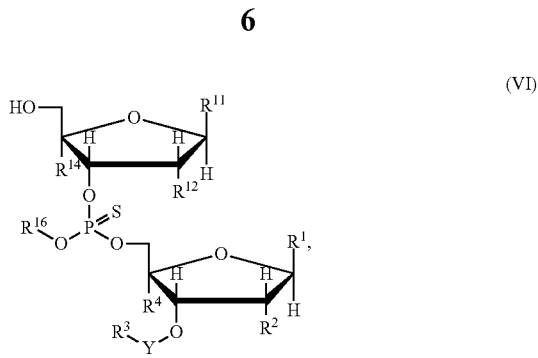

or a pharmaceutically acceptable salt thereof.

A third embodiment of the invention is a process as described for the second embodiment, further comprising the step of d) reacting the compound of Formula (VI) with a compound of Formula (II) to form a compound of Formula (VII):

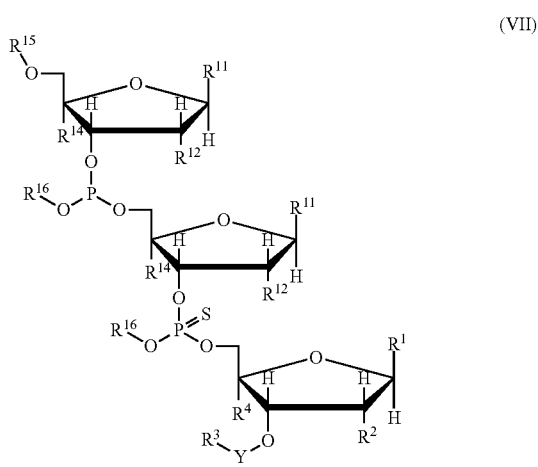

or a pharmaceutically acceptable salt thereof; and e) oxidizing the compound of Formula (VII) with a oxidizing agent to form a compound of Formula (VIII):

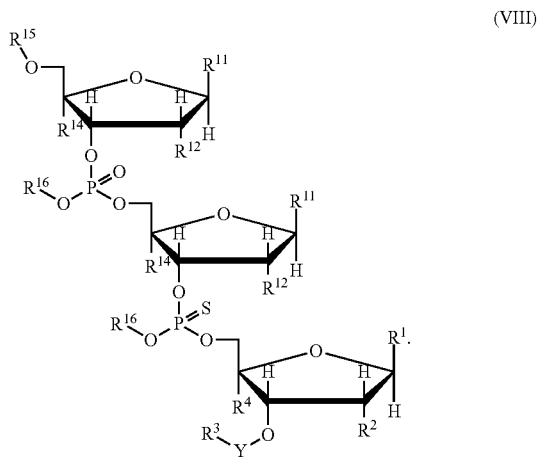

A fourth embodiment of the invention is a process as described for the third embodiment, further comprising the step of f) deprotecting the compound of Formula (VIII) to form the compound of Formula (IX):

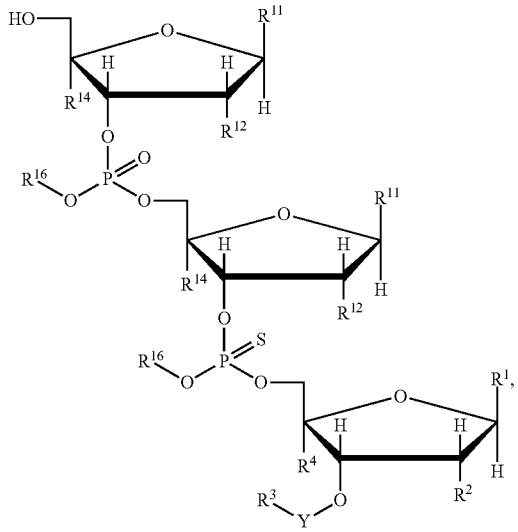

(IX)

or a pharmaceutically acceptable salt thereof.

A fifth embodiment of the invention is a process as described for the second and fourth embodiments, wherein starting with the compound of Formula (VI) or the compound of Formula (IX), steps a), b), and c) are repeated n times and steps d), e), and f) are repeated m times, wherein repetition of steps a), b), and c) and steps d), e) and f) can occur in any order relative to each other, wherein n is at least 1 or more and m is 0, 1, 2, 3, or 4, to form an oligonucleotide of Formula (X) or (XI):

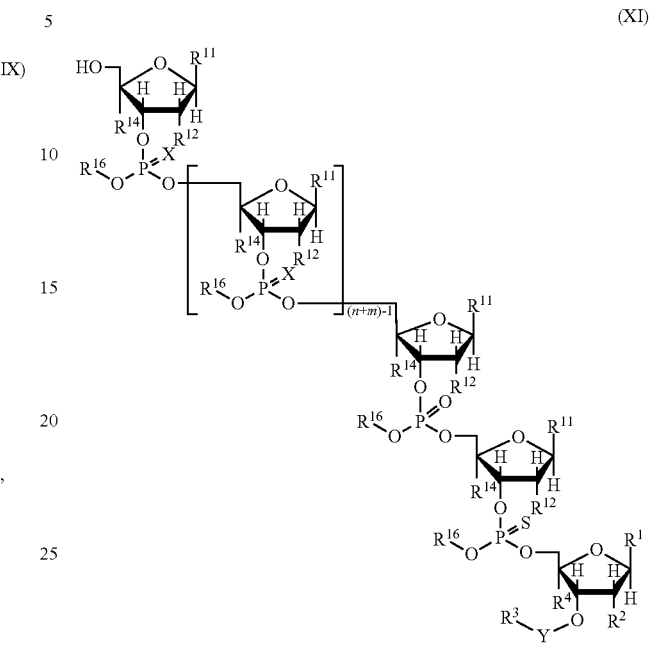

(XI)

or a pharmaceutically acceptable salt thereof, or forms a oligonucleotide wherein each repetition of steps a, b, and c, or steps d, e, and f results in some unreacted compound of Formula (VI) and (IX) that reacts with excess sulfurization agent or the byproduct of the sulfurization agent following the sulfurization step to form a compound of Formula (XII) or (XIII):

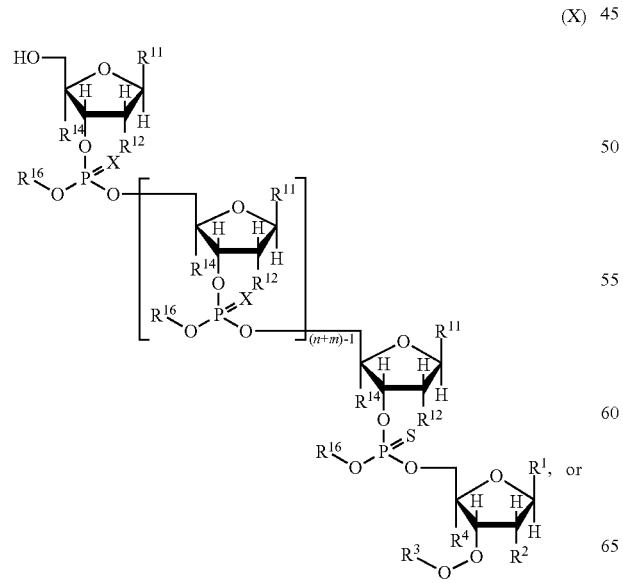

(X)

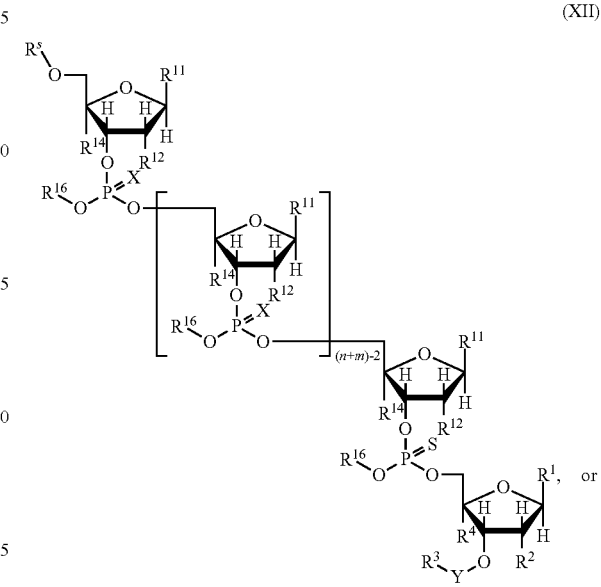

(XII)

-continued

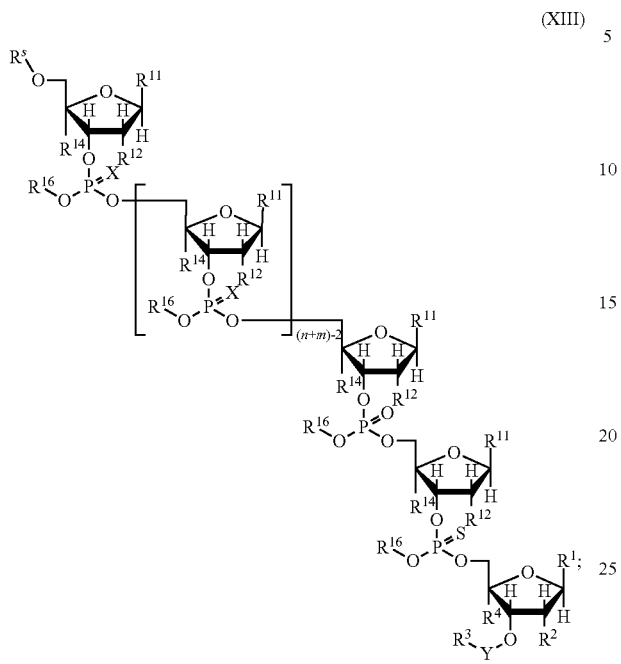

(XIII)

wherein each X is independently selected from S or O, provided that X is O only 4, 3, 2, 1, or 0 times in the compound of Formula (X), (XI), (XII), and (XIII). In particular, n is 1 to 30, 5 to 25, or 10 to 15 and m is 0, 1, 2, 3, or 4.

The process described above for the fifth embodiment involves a stepwise addition of nucleotides to form the desired oligonucleotide. Each of these steps involve three reactions to add the nucleotide to the growing oligonucleotide. In the first step (corresponding to steps a and d), the 5' end of a nucleoside (such as a compound of Formula (I)) is coupled to the 3' end of nucleotide (such as a compound of Formula (II)). Depending on whether the linkage between these two newly bonded nucleotides is to be a phosphothioate (i.e., a P=S bond, as in, for example, Formula (IV)) or a phosphodiester (i.e., a P=O bond, as in, for example, Formula (VIII)), the oligonucleotide is either sulfurized (step b) or oxidized (step e), respectively. Finally, the next 5'-hydroxy group is deprotected (steps c or f, and for example, Formulas (VI) and (IX)) and the process is repeated to add the next nucleoside. As described above "some unreacted compound of Formula (VI) and (IX)" means that even of the coupling steps a) or d) complete, some compound of Formula (VI) and (IX) remains unreacted and available for subsequent coupling reaction, which would result in an oligonucleotide missing an oligonucleotide relative to the desired oligonucleotide. As oligionucleotides missing just one oligonucleotide ("the N-1 impurity") relative to the desired oligonucleotide can be difficult to separate from the desired oligonucleotide, the capping of the unreacted 5-OH hydroxy is necessary to prevent the formation of the N-1 impurity. By "some" any amount is contemplated, for example, less than 20%, 15%, 10%, 5%, 4%, 3%, 2%, 1%, or 0.5% may remain.

Therefore, this process allows for the synthesis of an oligonucleotide with any number of phosphothioate bonds and up to four phosphodiester without the need for any capping step at all because any unreacted 5'-hydroxy groups will react with the sulfurization agent itself or a byproduct of the reaction of the sulfurization agent with the phosphorous atom in the linkage between two nucleosides. This is in contrast to the conventional synthesis, where a capping step to block any of the unreacted 5' OH is done following the coupling step.

A sixth embodiment of the invention is a process as described for the third embodiment, further comprising the step of g) reacting the unreacted compound of Formula (VI) with a capping agent to form the compound of Formula (XIV):

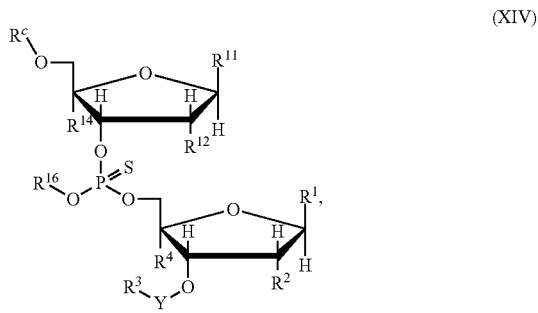

(XIV)

or a pharmaceutically acceptable salt thereof, wherein $R^c$ is s a hydroxy protecting group formed from the capping agent. A "capping agent" may be any capping agent known to one of skill in the art, for example, acetic anhydride with base catalysts, such as pyridine or N-methyl morpholine.

A seventh embodiment of the invention is a process as described for the sixth embodiment, further comprising the step of h) deprotecting the compound of Formula (VIII) to form the compound of Formula (XV):

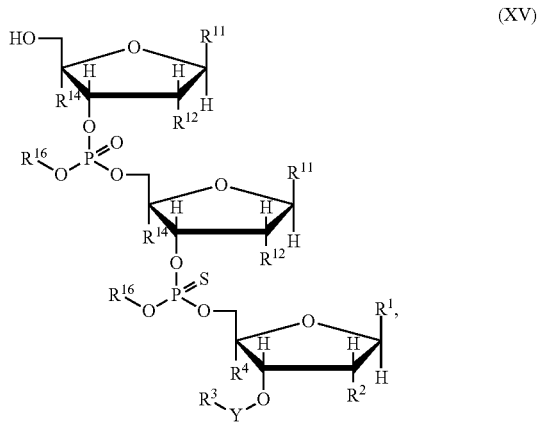

(XV)

or a pharmaceutically acceptable salt thereof.

A eighth embodiment of the invention is a process as described for the seventh embodiment, wherein starting with the compound of Formula (VI) or the compound of Formula (IX), steps a), b), and c) are repeated n times and steps d), e), g) and h) are repeated m times, wherein repetition of steps a), b), and c) and steps d), e), g) and h) can occur in any order relative to each other, wherein n is at least 1 and m is 0 or greater to form an oligonucleotide of Formula (X) or (XVII):

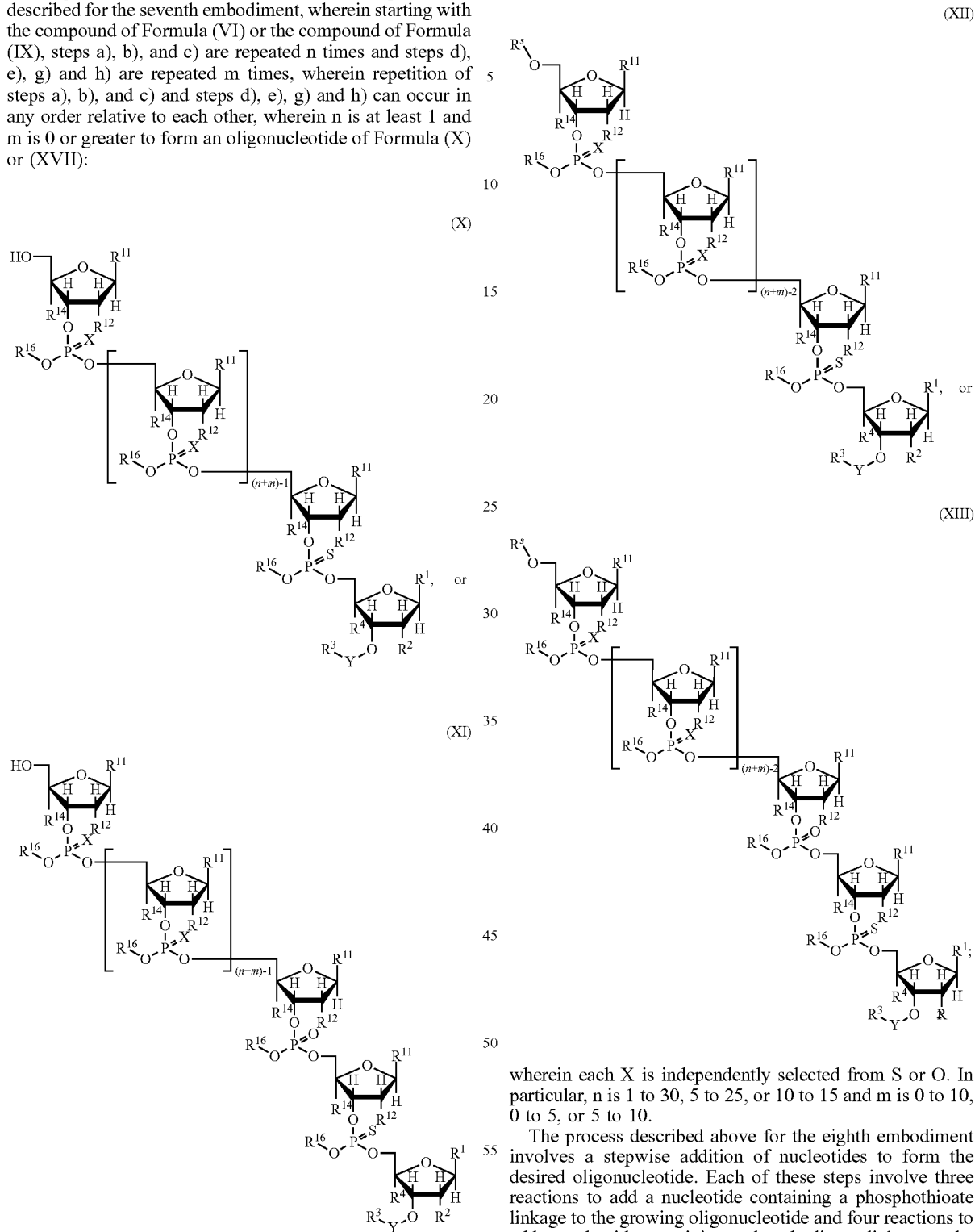

or a pharmaceutically acceptable salt thereof, or forms a oligonucleotide wherein each repetition of steps a, b, and c, or steps d, e, and f results in some unreacted compound of Formula (VI) and (IX) that reacts with excess sulfurization agent or the byproduct of the sulfurization agent following the sulfurization step to form a compound of Formula XII or XIII:

wherein each X is independently selected from S or O. In particular, n is 1 to 30, 5 to 25, or 10 to 15 and m is 0 to 10, 0 to 5, or 5 to 10.

The process described above for the eighth embodiment involves a stepwise addition of nucleotides to form the desired oligonucleotide. Each of these steps involve three reactions to add a nucleotide containing a phosphothioate linkage to the growing oligonucleotide and four reactions to add a nucleotide containing a phosphodiester linkage to the growing oligonucleotide. In the first step (corresponding to steps a and d,), the 5' end of a nucleoside (such as a compound of Formula I) is coupled to the 3' end of nucleotide (such as a compound of Formula II) to couple these two nucleotides (forming compounds such as those of Formula (III) and (VII). Depending on whether the linkage between these two newly bonded nucleotides is to be a phosphothioate (i.e., a P=S bond) or a phosphodiester (i.e., a P=O bond), the oligonucleotide is either sulfurized (step b, forming compound such as those of Formula (IV)) or oxidized (step e, forming compound such as those of Formula (IV) or (VIII)). Unlike the process described above for the fifth embodiment, as the eighth embodiment permits an unlimited number of phosphodiester linkages, a capping step must be completed following each oxidation step (step g). However, as for the fifth embodiment, no capping step is required following the sulfurization step. As for the fifth embodiment, the next 5'-hydroxy group is deprotected (steps c or h, and for example, Formulas (VI) and (IX)) and the process is repeated to add the next nucleoside. Therefore, this process allows for the synthesis of an oligonucleotide with any number of phosphothioate bonds and phosphodiester bond, and requires a capping step only after the cycle including an oxidation step. This is in contrast to the conventional synthesis, where a capping step to block any of the unreacted 5'OH is done every cycle, even those including a sulfurization step.

In some aspects of the first, second, third, fourth, fifth, sixth, seventh, and eight embodiments, the compounds of Formulas (I), (II), (III), (IV), (V), (VI), (VII), (VIII), (IX), (X), (XI), (XII), (XIII), (XIV), or (XV) are not salts.

In a particular aspect of the fifth or eighth embodiments, n is 2 to 1000. In particular, n is 2 to 500. In particular, n is 2 to 50. In particular, n is 2 to 25.

In a ninth embodiment, the process is as described for any one of the first, second, third, fourth, fifth, sixth, seventh, and eighth embodiments, or any aspect thereof, wherein the linker attached to the solid support is cleaved.

In a tenth embodiment, the process is as described for any one of the first, second, third, fourth, fifth, sixth, seventh, eighth, and ninth embodiments, or any aspect thereof, the sulfurization agent is a compound of Formula A:

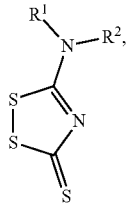

(A)

wherein each of $R^1$ and $R^2$ are independently selected from H, an optionally substituted alkyl and an optionally substituted aryl group. In a particular aspect of the tenth embodiment, $R^1$ and $R^2$ are both H:

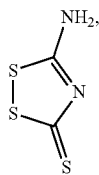

which is known as 3-amino-1,2,4-dithiazole-5-thione (XH or ADTT). In some aspects, $R^S$ is —C(SH)(=N)—CN.

In a particular aspect of the tenth embodiment, $R^1$ and $R^2$ are both methyl:

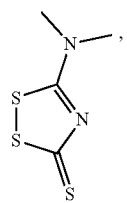

which is known as 3-(N,N-dimethylamino-methylidene) amino)-3H-1,2,4-dithiazole (DDTT). In some aspects, $R^S$ is —C(=S)NHC(=S)N=CHN(CH$_3$)$_2$.

In an eleventh embodiment, the process is as described for any one of the first, second, third, fourth, fifth, sixth, seventh, eighth, and ninth embodiments, or any aspect thereof, the sulfurization agent is a compound of Formula B:

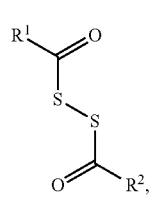

(B)

wherein each of $R^1$ and $R^2$ are independently selected from H, an optionally substituted alkyl and an optionally substituted aryl group. In a particular aspect of the tenth embodiment, $R^1$ and $R^2$ are both benzyl (PhCH$_2$):

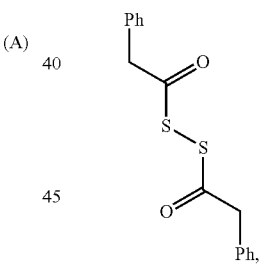

which is known as phenylacetyl disulfide (PADS). In a particular aspect, and $R^S$ is —C(=O)CH$_2$C$_6$H$_5$.

In a twelfth embodiment, the process is as described for any one of the first, second, third, fourth, fifth, sixth, seventh, eighth, and ninth embodiments, or any aspect thereof, the sulfurization agent is 3H-1,2-benzodithiol-3-one 1,1-dioxide (Beaucage Reagent):

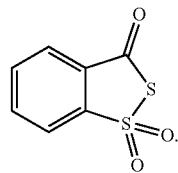 [SMILES: O=C1SS(=O)(=O)c2ccccc21]

In a specific aspect of the twelfth embodiment, $R^S$ is

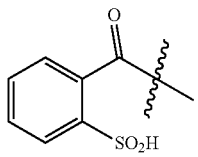

In a thirteenth embodiment, the process is as described for any one of the first, second, third, fourth, fifth, sixth, seventh, eighth, ninth, tenth, eleventh, and twelfth embodiments, or any aspect thereof, wherein the sulfurization agent is reacted by recirculating the sulfurization agent for 0 to 30 minutes, for example, 0, 5, 10, 15, 20, 25, or 30 minutes. In one embodiment, the sulfurization agent is recirculated for 1 to 30 minutes, 1 to 20 minutes, 1 to 10 minutes, or 1 to 5 minutes. In another embodiment, the sulfurization agent is recirculated for 1, 2, 3, 4, 5, 6, 7, 8, 9, or 10 minutes.

In a fourteenth embodiment, the process is as described for any one of the first, second, third, fourth, fifth, sixth, seventh, eighth, ninth, tenth, eleventh, twelfth, and thirteenth embodiments, or any aspect thereof, wherein the sulfurization agent is recirculated at least 0-20 times, for example, 1, 2, 5, 10, 15, 20 times. In one embodiment, the sulfurization agent is recirculated for 1-20 times, 1-10 times, or 1-5 times.

In a fifteenth embodiment, the process is as described for any one of the first, second, third, fourth, fifth, sixth, seventh, eighth, ninth, tenth, eleventh, twelfth, thirteenth, and fourteenth embodiments, or any aspect thereof, the sulfurization agent is reacted by recirculating 3 to 6 equivalents of sulfurization agent relative to the amount of the first nucleoside attached to the solid support.

In a sixteenth embodiment, the process is as described for any one of the first, second, third, fourth, fifth, sixth, seventh, eighth, ninth, tenth, eleventh, twelfth, thirteenth, fourteenth, and fifteenth embodiments, or any aspect thereof, the concentration of the sulfurization reagent is from 0.02 M to 2.0 M. In some aspects, the sulfurization agent is dissolved in pyridine, 3-piccoline, acetonitrile, or a mixture thereof. In a particular aspect of the sixteenth embodiment, the concentration of the sulfurization reagent is from 0.05 M to 0.5 M. In a particular aspect, the sulfurization reagent is 3-(dimethylamino-methylidene)amino)-3H-1,2,4-dithiazole (DDTT) added at a concentration of 0.02 M to 0.1 M, for example, 0.02, 0.03, 0.04, 0.05, 0.06, 0.07, 0.08, 0.09, or 0.1M dissolved in pyridine. In a particular aspect, the sulfurization reagent is 3H-1,2-benzodithiol-3-one 1,1-dioxide (Beaucage Reagent) added at a concentration of 0.01 M to 0.2 M, for example, 0.01, 0.02, 0.03, 0.04, 0.05, 0.06, 0.07, 0.08, 0.09, 0.10, 0.11, 0.12, 0.13, 0.14, 0.15, 0.16, 0.17, 0.18, 0.19, 0.2 M in acetonitrile (ACN). In a particular aspect, the sulfurization reagent is phenylacetyl disulfide (PADS) added at a concentration of 0.01 M to 0.2 M, for example, 0.01, 0.02, 0.03, 0.04, 0.05, 0.06, 0.07, 0.08, 0.09, 0.10, 0.11, 0.12, 0.13, 0.14, 0.15, 0.16, 0.17, 0.18, 0.19, 0.2 M in acetonitrile (ACN)/3-picoline. In a particular aspect, the sulfurization reagent is 3-amino-1,2,4-dithiazole-5-thione (XH or ADTT) added at a concentration of 0.01 M to 0.2 M, for example, 0.01, 0.02, 0.03, 0.04, 0.05, 0.06, 0.07, 0.08, 0.09, 0.10, 0.11, 0.12, 0.13, 0.14, 0.15, 0.16, 0.17, 0.18, 0.19, 0.2 M in pyridine.

In certain embodiments, the sulfurization reagent described above (e.g., phenylacetyl disulfide (PADS) or 3-amino-1,2,4-dithiazole-5-thione (XH)) is treated with a base (i.e., aging) prior to its use in the process of the present invention. Exemplary base includes, but is not limited to, N-methylimidazole, pyridine and 3-picoline. The sulfurization reagent can be aged with the base (i.e., treated with the base) for 1 minute to 5 days, for example for 5 minutes to 24 hours, 10 minutes to 12 hours, 30 minutes to 10 hours, 1 hour to 8 hours, 2 hours to 6 hours, or 3 hours to 5 hours. In one embodiment, the sulfurization reagent is aged for 4 hours. In another embodiment, the sulfurization reagent PADS is aged with 3-picoline for 4 hours before being used in the process of the present invention.

In a seventeenth embodiment, the process is as described for any one of the first, second, third, fourth, fifth, sixth, seventh, eighth, ninth, tenth, eleventh, twelfth, thirteenth, fourteenth, fifteenth, and sixteenth embodiments, or any aspect thereof, the nucleobase is selected from the group consisting of cytosine, guanine, adenine, thymine (or 5-methyl uracil), uracil, hypoxanthine, xanthine, 7-methylguanine, 5,6-dihydrouracil, 5-methylcytosine, and 5-hydroxymethylcytosine, wherein the $NH_2$ group of the nucleobase, if present, is protected by PhCO—, $CH_3$CO—, iPrCO—, $Me_2$N—CH=, or $Me_2$N—CMe=. In a particular embodiment, the nucleobase is selected from the group consisting of cytosine, guanine, adenine, thymine (or 5-methyl uracil), uracil, and 5-methylcytosine, wherein the $NH_2$ group of the nucleobase, if present, is protected by PhCO—, $CH_3$CO—, iPrCO—, $Me_2$N—CH=, or $Me_2$N—CMe=.

In an eighteenth embodiment, the process is as described for any one of the first, second, third, fourth, fifth, sixth, seventh, eighth, ninth, tenth, eleventh, twelfth, thirteenth, fourteenth, fifteenth, sixteenth, and seventeenth embodiments, or any aspect thereof, each $R^2$ and $R^{12}$ are independently selected from the group consisting of H, F, and $C_{1-4}$ alkoxy optionally substituted with $C_{1-4}$ alkoxy; each $R^4$ is independently H or forms a ring with the alkoxy group of $R^2$, wherein the ring is a 5 or 6-membered ring optionally substituted with 1 to 3 $C_{1-4}$ alkyl groups; $R^{16}$ is —$CH_2CH_2CN$; $R^{17a}$ and $R^{17b}$ are independently $C_{1-4}$ alkyl; and each $R^{14}$ is independently H or forms a ring with the alkoxy group of $R^{12}$, wherein the ring is a 5 or 6-membered ring optionally substituted with 1 to 3 $C_{1-4}$ alkyl groups.

In a nineteenth embodiment, the process is as described for any one of the first, second, third, fourth, fifth, sixth, seventh, eighth, ninth, tenth, eleventh, twelfth, thirteenth, fourteenth, fifteenth, sixteenth, seventeenth and eighteenth embodiments, or any aspect thereof, each $R^2$ and $R^{12}$ are independently selected from H or $C_{1-4}$ alkoxy optionally substituted with $C_{1-4}$ alkoxy; $R^{15}$ is 4,4'-dimethoxytrityl; $R^{16}$ is —$CH_2CH_2CN$; $R^{17a}$ and $R^{17b}$ are independently $C_{1-6}$ alkyl; and $R^S$ is —C(=N)(SH)—CN or —C(=O)$CH_2C_6H_5$.

In a twentieth embodiment, the process is as described for any one of the first, second, third, fourth, fifth, sixth, seventh, eighth, ninth, tenth, eleventh, twelfth, thirteenth, fourteenth, fifteenth, sixteenth, seventeenth, eighteenth, and nineteenth embodiments, or any aspect thereof, Y is absent. Alternatively, Y is a single nucleotide. Alternatively, Y is oligonucleotide comprising 2 to 50 nucleotides, in particular, 2 to 40 nucleotides, 2 to 30 nucleotides, or 2 to 25 nucleotides.

In a twenty-first embodiment, the process is as described for any one of the first, second, third, fourth, fifth, sixth, seventh, eighth, ninth, tenth, eleventh, twelfth, thirteenth, fourteenth, fifteenth, sixteenth, seventeenth, eighteenth, nineteenth, and twentieth embodiments, or any aspect thereof, the compound of Formula (X) or (XI) is an antisense oligonucleotide comprising 2 to 30 nucleotides. In a particular aspect, the anti-sense oligonucleotide comprises modified RNA only. Alternatively, the anti-sense oligonucleotide comprises DNA and modified RNA. In particular, the anti-sense oligonucleotide is a gapmer. Alternatively, the anti-sense oligonucleotide comprises DNA only.

In a twenty-second embodiment, the process is as described for any one of the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, and twenty-first embodiments, or any aspect thereof, the anti-sense oligonucleotide is a phosphorothioate oligonucleotide having a sequence of (from 5' to 3')

TCACTTTCATAATGCTGG, (SEQ ID NO: 1)

wherein each internucleoside linkage of the oligonucleotide is a phosphorothioate linkage, each nucleoside of the oligonucleotide is a 2'-O— methoxyethyl (MOE) nucleoside, and each cytosine is a 5-methylcytosine. SEQ ID NO: 1 is also known as BIIB058, and is described in WO2007/002390, WO2010/148249, and U.S. Pat. No. 8,980,853, the teaching of each are herein incorporated by reference.

In a twenty-third embodiment, the process is as described for any one of the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, and twenty-first embodiments, or any aspect thereof, the sequence of the anti-sense oligonucleotide is a 5-10-5 MOE gapmer, having a sequence of (from 5' to 3')

CAGGATACATTTCTACAGCT, (SEQ ID NO: 2)

wherein each of nucleosides 1-5 and 16-20 are 2'-O-methoxyethylribose modified nucleosides, and each of nucleosides 6-15 are 2'-deoxynucleosides, wherein the internucleoside linkages between nucleosides 2 to 3, 4 to 5, 16 to 17, and 18 to 19 are phosphodiester linkages and the internucleoside linkages between nucleosides 1 to 2, 3 to 4, 5 to 6, 6 to 7, 7 to 8, 8 to 9, 9 to 10, 10 to 11, 11 to 12, 12 to 13, 13 to 14, 14 to 15, 15 to 16, 17 to 18, and 19 to 20 are phosphorothioate linkages, and wherein each cytosine is a 5'-methylcytosine. SEQ ID NO:2 is described by the following chemical notation: mCes Aeo Ges Geo Aes Tds Ads mCds Ads Tds Tds Tds mCds Tds Ads mCeo Aes Geo mCes Te;

wherein,

A=an adenine, mC=a 5'-methylcytosine

G=a guanine,

T=a thymine, e=a 2'-O-methoxyethylribose modified sugar, d=a 2'-deoxyribose sugar, s=a phosphorothioate internucleoside linkage, and o=a phosphodiester internucleoside linkage.

SEQ ID NO: 2 is as known as BIIB067 or ISIS 666853 and is described in WO2015153800, the teachings of which are incorporated herein by reference.

In a twenty-fourth embodiment, the process is as described for any one of the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, and twenty-first embodiments, or any aspect thereof, the anti-sense oligonucleotide is a 4-8-6 gapmer, having a sequence of (from 5' to 3'):

GCCCCTAGCGCGCGACUC (SEQ ID NO: 8)

wherein each of nucleosides 1-4 and 13-18 are 2'-O-methoxyethylribose modified nucleosides, and each of nucleosides 5-12 are 2'-deoxy ribonucleotides, wherein the internucleoside linkages between nucleosides 2 to 3, 3 to 4, 13 to 14, 14 to 15, and 15 to 16 are phosphodiester linkages and the internucleoside linkages between nucleosides 1 to 2, 4 to 5, 5 to 6, 6 to 7, 7 to 8, 8 to 9, 9 to 10, 10 to 11, 11 to 12, 12 to 13, 16 to 17 and 17 to 18 are phosphorothioate linkages, wherein each cytosine is 5-methylcytosine, and wherein the uracil is 5-methyluracil. SEQ ID NO:8 is described by the following chemical notation:

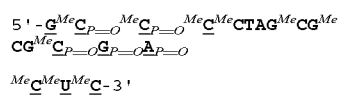

Underline=MoE ribonucleotide

G=guanine $^{Me}$C=5-methylcytosine

T=thymine

A=adenine $^{Me}$U=5-methyluracil (also known as thymine)

P=O=phosphodiester internucleoside linkage

Any other internucleoside linkages are phosphothioester linkage.

An "amine protecting group" includes any group suitable for protecting an amine group, $NH_2$, for example, but not limited to, PhCO—, $CH_3$CO—, iPrCO—, and $Me_2$N—CH=, $Me_2$N—CMe=. The resulting structure of an amino group protected by $Me_2$N—CH= and $Me_2$N—CMe= is as follows:

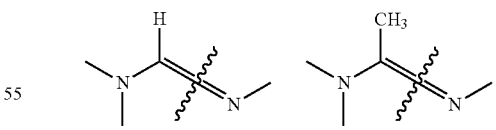

Further amine protecting groups can be found in Greene, T W et al., *Protective Groups in Organic Synthesis*, 4th Ed., John Wiley and Sons (2007).

Without wishing to be bound by theory, it is thought that the 5'-hydroxy that failed to couple during the coupling step forms a hydroxyl derivative from sulfurization with the sulfurization agent, such as, for example, PADS, or a N-cyanocarbonimidothioate from xanthane hydride, or N,N-dimethylthiourea-N-thiocarboxylate from DDTT:

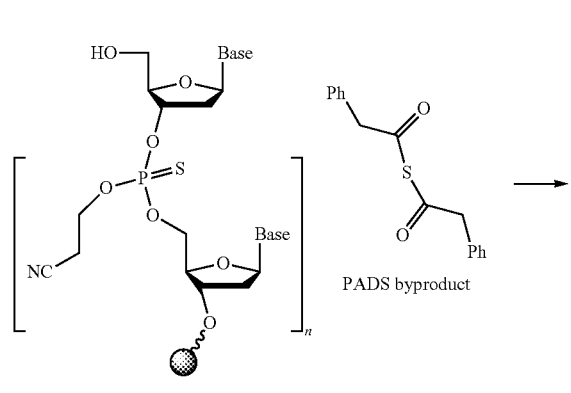

failure sequence

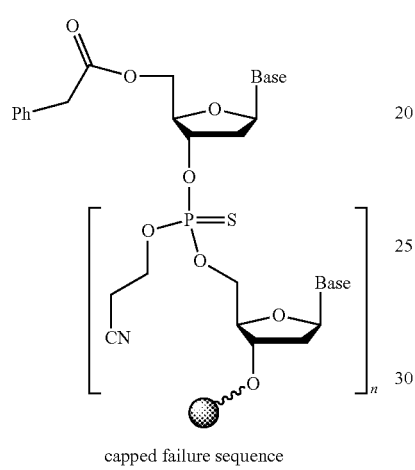

capped failure sequence

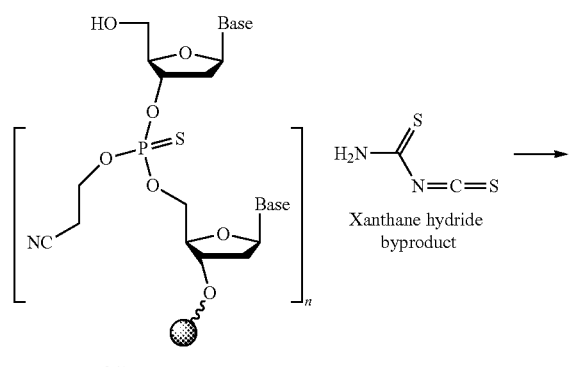

failure sequence

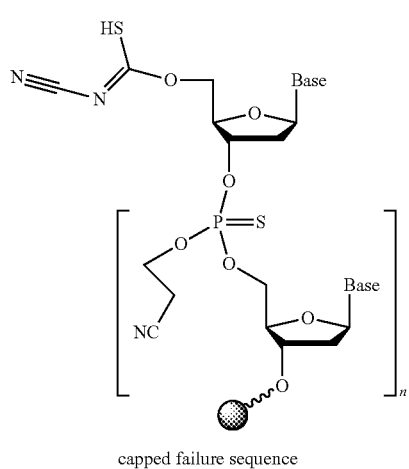

capped failure sequence

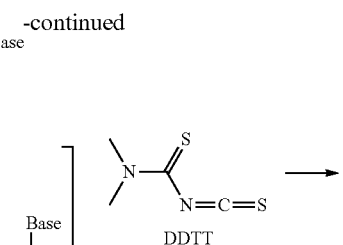

failure sequence

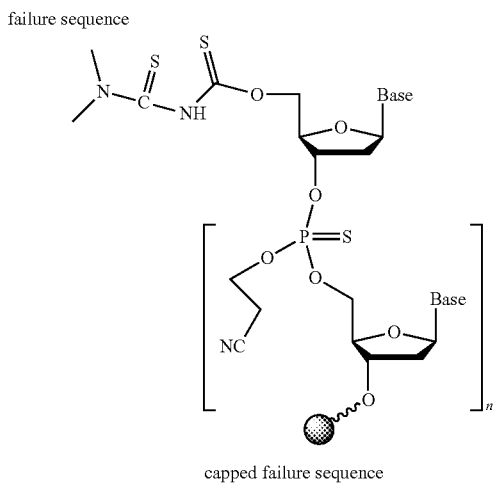

capped failure sequence

A "hydroxy protecting group" includes any group suitable for protecting a hydroxy group, OH. These protecting groups and further examples of hydroxy protecting groups can be found in Greene, T W et al., *Protective Groups in Organic Synthesis*, 4th Ed., John Wiley and Sons (2007).

In a specific embodiment, the hydroxy protecting group is formed from the capping agent (e.g., $R^c$ in Formula (XIV)), and can be selected from, for example, acetyl (Ac); benzoyl (Bz); benzyl (Bn); β-methoxyethoxymethyl ether (MEM); methoxymethyl ether (MOM); methoxytrityl [(4-methoxyphenyl)diphenylmethyl, MMT); p-methoxybenzyl ether (PMB); methylthiomethyl ether; pivaloyl (Piv); tetrahydropyranyl (THP); tetrahydrofuran (THF); silyl ether (including, but not limited to, trimethylsilyl (TMS), tert-butyldimethylsilyl (TBDMS), tri-iso-propylsilyloxymethyl (TOM), and triisopropylsilyl (TIPS) ethers); methyl ethers, and ethoxyethyl ethers (EE).

Alternatively, the hydroxy protecting group blocks a 5'-hydroxy of a nucleoside or nucleotide (e.g., $R^{15}$ in Formulas (II), (III), (IV), (VII), and (VIII)), and in particular aspect is an acid-labile protecting group selected from 4,4'-dimethoxytrityl, [bis-(4-methoxyphenyl)phenylmethyl] (DMT) or trityl (triphenylmethyl, Tr).

"Nucleobase" means the heterocyclic base portion of a nucleoside. Nucleobases may be naturally occurring or may be modified. In certain embodiments, a nucleobase may comprise any atom or group of atoms capable of hydrogen bonding to a nucleobase of another nucleic acid. In particular, the nucleobase is a heterocyclic base, typically purines and pyrimidines. In addition to "unmodified" or "natural" nucleobases such as the purine nucleobases adenine (A) and guanine (G), and the pyrimidine nucleobases thymine (T), cytosine (C) and uracil (U), many modified nucleobases or nucleobase mimetics known to those skilled in the art are amenable to incorporation into the compounds synthesized by the method described herein. In certain embodiments, a modified nucleobase is a nucleobase that is fairly similar in structure to the parent nucleobase, such as for example a 7-deaza purine, a 5-methyl cytosine, or a G-clamp. In certain embodiments, nucleobase mimetic include more complicated structures, such as for example a tricyclic phenoxazine nucleobase mimetic. Methods for preparation of the above noted modified nucleobases are well known to those skilled in the art.

"Nucleoside" means a compound comprising a heterocyclic base moiety and a sugar moiety.

"Nucleotide" means a nucleoside comprising a phosphate linking group.

"Oligonucleotide" refers to a compound comprising a plurality of linked nucleosides. In certain embodiments, one or more of the plurality of nucleosides is modified. In certain embodiments, an oligonucleotide comprises one or more ribonucleosides (RNA) and/or deoxyribonucleosides (DNA).

"Internucleoside linkage" means a covalent linkage between adjacent nucleosides of an oligonucleotide.

"Gapmer" means a chimeric antisense compound in which an internal region having a plurality of nucleosides that support RNase H cleavage is positioned between external regions having one or more nucleosides, wherein the nucleosides comprising the internal region are chemically distinct from the nucleoside or nucleosides comprising the external regions.

As used herein, the term "alkyl" refers to a fully saturated branched or unbranched hydrocarbon moiety. Preferably the alkyl comprises 1 to 20 carbon atoms, more preferably 1 to 16 carbon atoms, 1 to 10 carbon atoms, 1 to 6 carbon atoms, or 1 to 4 carbon atoms. In some embodiments, an alkyl comprises from 6 to 20 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, or n-decyl.

The term "aryl" refers to monocyclic, bicyclic or tricyclic aromatic hydrocarbon groups having from 6 to 14 carbon atoms in the ring portion. In one embodiment, the term aryl refers to monocyclic and bicyclic aromatic hydrocarbon groups having from 6 to 10 carbon atoms. Representative examples of aryl groups include phenyl, naphthyl, fluorenyl, and anthracenyl.

The term "aryl" also refers to a bicyclic or tricyclic group in which at least one ring is aromatic and is fused to one or two non-aromatic hydrocarbon ring(s). Nonlimiting examples include tetrahydronaphthalene, dihydronaphthalenyl and indanyl.

Optional substituents for both the alkyl or aryl groups are, in each occurrence, independently selected from $C_{1-6}$alkyl, $C_{2-6}$alkenyl, $C_{2-6}$alkynyl, 3- to 7-membered carbocyclyl, 3- to 7-membered heterocyclyl, halo, —CN, —C(O)R$^a$, —C(O)$_2$R$^a$, —C(O)N(R$^a$)$_2$, —OR$^a$, —N(R$^a$)$_2$, —N(R$^a$)C(O)R$^a$, —N(R$^a$)N(R$^a$)$_2$, —NO$_2$, —N(R$^a$)C(O)$_2$R$^a$, —N(R$^a$)C(O)N(R$^a$)$_2$, —N(R$^a$)S(O)$_2$R$^a$, —SR$^a$, —S(O)R$^a$, —S(O)$_2$R$^a$, —S(O)N(R$^a$)$_2$, and —S(O)$_2$N(R$^a$)$_2$; and R$^a$ in each occurrence is independently selected from H, $C_{1-6}$alkyl, 3- to 6-membered monocyclic carbocyclyl, and 3- to 6-membered monocyclic heterocyclyl.

As used herein, the term "carbocyclyl" refers to saturated or unsaturated monocyclic or bicyclic hydrocarbon groups of 3-7 carbon atoms, 3-6, or 5-7 carbon atoms. The term "carbocyclyl" encompasses cycloalkyl groups and aromatic groups. The term "cycloalkyl" refers to completely saturated monocyclic or bicyclic hydrocarbon groups of 3-7 carbon atoms, 3-6 carbon atoms, or 5-7 carbon atoms. Exemplary monocyclic carbocyclyl groups include, but are not limited to, cyclopropyl, cyclobutyl, cyclopentyl, cyclohexyl, cycloheptyl, cyclopropenyl, cyclobutenyl, cyclopenentyl, cyclohexenyl, cycloheptenyl, cyclobutadienyl, cyclopentadienyl, cyclohexadienyl, cycloheptadienyl, phenyl and cycloheptatrienyl. Exemplary bicyclic carbocyclyl groups include bicyclo[2.1.1]hexyl, bicyclo[2.2.1]heptyl, bicyclo[2.2.1]heptenyl, tricyclo[2.2.1.0$^{2,6}$]heptanyl, 6,6-dimethylbicyclo[3.1.1]heptyl, or 2,6,6-trimethylbicyclo[3.1.1]heptyl, spiro[2.2]pentanyl, and spiro[3.3]heptanyl.

The term "bridged ring system," as used herein, is a ring system that has a carbocyclyl or heterocyclyl ring wherein two non-adjacent atoms of the ring are connected (bridged) by one or more (preferably from one to three) atoms selected from C, N, O, or S. A bridged ring system may have from 6-7 ring members.

The term "spiro ring system," as used herein, is a ring system that has two rings each of which are independently selected from a carbocyclyl or a heterocyclyl, wherein the two ring structures having one ring atom in common. Spiro ring systems have from 5 to 7 ring members.

As used herein, the term "heterocyclyl" refers to a saturated or unsaturated, monocyclic or bicyclic (e.g., bridged or spiro ring systems) ring system which has from 3- to 7-ring members, or in particular 3- to 6-ring members or 5- to 7-ring members, at least one of which is a heteroatom, and up to 4 (e.g., 1, 2, 3, or 4) of which may be heteroatoms, wherein the heteroatoms are independently selected from O, S and N, and wherein C can be oxidized (e.g., C(O)), N can be oxidized (e.g., N(O)) or quaternized, and S can be optionally oxidized to sulfoxide and sulfone. Unsaturated heterocyclic rings include heteroaryl rings. As used herein, the term "heteroaryl" refers to an aromatic 5 or 6 membered monocyclic ring system, having 1 to 4 heteroatoms independently selected from O, S and N, and wherein N can be oxidized (e.g., N(O)) or quaternized, and S can be optionally oxidized to sulfoxide and sulfone. In one embodiment, a heterocyclyl is a 3- to 7-membered saturated monocyclic or a 3- to 6-membered saturated monocyclic or a 5- to 7-membered saturated monocyclic ring. In one embodiment, a heterocyclyl is a 3- to 7-membered monocyclic or a 3- to 6-membered monocyclic or a 5- to 7-membered monocyclic ring. In another embodiment, a heterocyclyl is a 6 or -7-membered bicyclic ring. The heterocyclyl group can be attached at a heteroatom or a carbon atom. Examples of heterocyclyls include aziridinyl, oxiranyl, thiiranyl, oxaziridinyl, dioxiranyl, azetidinyl, oxetanyl, thietanyl, pyrrolidinyl, tetrahydrofuranyl, thiolanyl, imidazolidinyl, pyrazolidinyl, oxazolidinyl, isoxazolidinyl, thiazolidinyl, isothiazolidinyl, dioxolanyl, dithiolanyl, oxathiolanyl, piperidinyl, tetrahydropyranyl, thianyl, piperazinyl, morpholinyl, thiomorpholinyl, dioxanyl, dithianyl, trioxanyl, trithianyl, azepanyl, oxepanyl, thiepanyl, dihydrofuranyl, imidazolinyl, dihydropyranyl, and heteroaryl rings including azirinyl, oxirenyl, thiirenyl, diazirinyl, azetyl, oxetyl, thietyl, pyrrolyl, furanyl, thiophenyl (or thienyl), imidazolyl, pyrazolyl, oxazolyl, isoxazolyl, thiazolyl, isothiazolyl, furazanyl, oxadiazolyl, thiadiazolyl, dithiazolyl, triazolyl, tetrazolyl, pyridinyl, pyranyl, thiopyranyl, pyrazinyl, pyrimidinyl, pyridazinyl, oxazinyl, thiazinyl, dioxinyl, dithiinyl, oxathianyl, triazinyl, tetrazinyl, azepinyl, oxepinyl, thiepinyl, diazepinyl, and thiazepinyl and the like. Examples of bicyclic heterocyclic ring systems include 3-azabicyclo[3.1.0]hexanyl, 3-azabicyclo[3.1.1]heptanyl, 2-azaspiro[3.3]heptanyl, 2-oxa-6-azaspiro[3.3]heptanyl, and 5-azaspiro[2.3]hexanyl.

"Halogen" or "halo" may be fluoro, chloro, bromo or iodo.

EXEMPLIFICATION

Example 1 Oligonucleotide Synthesis

Oligonucleotides were synthesized on 0.72-2.2 mmol scale using an AKTA 100 solid-phase synthesizer with Nittophase HL Unylinker (Kinovate, loading 350 μmol/g) as the solid support. The synthesis cycle for attaching each nucleoside consists of three reaction steps: detritylation, coupling, and sulfurization. The detritylation step was accomplished with dichloroacetic acid in toluene (10%) as the reagent. The coupling step was carried out by circulating a solution of corresponding phosphoramidite (0.1-0.2 M in acetonitrile) and 4,5-dicyanoimidazole (1.0 M in acetonitrile containing 0.1M N-methylimidazole) through the solid support. The sulfurization step was completed by circulating any one of the following solutions: (a) 0.2 M PADS in acetonitrile/3-picoline (1:1, v/v); (b) 0.2 M 3-Amino-1,2,4-dithiazole-5-thione (XH) in Pyridine; (c) 0.2 M 3H-1,2-Benzodithiol-3-one 1,1-Dioxide (Beaucage Reagent) in Acetonitrile; or (d) 0.1 M 3-((Dimethylamino-methylidene)amino)-3H-1,2,4-dithiazole-3-thione (DDTT) in Pyridine. For the control experiments, the synthesis consists of four reaction steps: detritylation, coupling, and sulfurization, and capping step. All the steps are carried out the same way as above, except with a capping step after the sulfurization step. The capping was done with a mixture of acetic anhydride, pyridine, and N-methyl imidazole in acetonitrile. Cleavage of the oligonucleotides from the support and base deprotection were performed in concentrated ammonium hydroxide at elevated temperature (50 to 60° C.). The synthesis reaction parameters are summarized in Table 1 below. The oligonucleotide products were analyzed by LC-MS.

TABLE 1

Process Protocol

| Process Step | Variable | 3-reactions-cycle | 4-reactions-cycle | | Units |
|---|---|---|---|---|---|
| Synthesis Support | Support | Nittophase Unylinker HL | Nittophase Unylinker HL | | μmol/g |
| | Loading | 350 | 350 | | μmol/g |
| Detritylation | Reagent | 10% DCA | 10% DCA | | |
| | Deblock Volume | 3 | 3 | | CV* |
| | Reaction Time | 3-6 | 3-6 | | Min |
| Coupling | Eq amidite | 1.5 | 1.5 | | eq** |
| | Conc. Amidite | 0.2 | 0.2 | | M |
| | Activator: amidite ratio | 5:1 | 5:1 | | |
| | Activator | DCI [1.0M] and NMI [0.1M] | DCI [1.0M] and NMI [0.1M] | | |
| | Recycle Flow Rate | 240 | 240 | | cm/hr |
| | Recycle Time | 3.2 | 3.2 | | min |
| Sulfurization | Reagent | 0.2M PADS in ACN/3-picoline (1:1, v/v) or 0.2M XH in Pyridine or 0.2M Beaucage Reagent in ACN or 0.1M DDTT in Pyridine | 0.2M PADS in ACN/3-picoline (1:1, v/v) | 0.2M XH in pyridine | |
| | Charge Volume | 1.1 | 1.2 | 1.1 | CV |
| | Reaction Time | Recycle mode 5 | Flow through mode 3.3 | Recycle or flow through mode 5 | min |
| Oxidation | Reagent | 0.5M Iodine in water/pyridine | 0.5M Iodine in water/pyridine | | |
| | Charge Volume | 2.0 | 2.0 | | CV |
| | ContactTime | 5 | 5 | | min |
| Capping | Reagent | NONE | Cap A, 2:3:5 [NMI/pyridine/ACN] Cap B 1:4 [Ac₂O/ACM] | | |
| | Capping Charge Volume | | 0.3 | | CV |

TABLE 1-continued

| | Process Protocol | | | |
|---|---|---|---|---|
| Process Step | Variable | 3-reactions-cycle | 4-reactions-cycle | Units |
| | Reaction Time | | 3-8 | min |
| Phosphorus Deprotection | Reagent | 50% TEA | 50% TEA | |
| | Charge Volume | 1.6 | 1.6 | CV |
| | Reaction Time | 90 | 90 | min |

*CV: column volume
**eq.: equivalent

Oligonucleotides Prepared by Process:

1. BIIB 058 (SEQ ID NO: 1), an 18-mer phosphorothioate oligonucleotide, in which each ribooligonucleotide includes methoxy-ethyl (MoE) at the 2' position.

underline: MoE ribonucleotide

P=O: phosphodiester any others: phosphothioester

TABLE 2

| | Phosphorothioate oligonucleotides A, B, C, D, and E | |
|---|---|---|
| Code | Sequence Type | Phosphorothioate Oligonucleotide Sequence |
| A | Fully DNA sequence | $^{Me}$CGA$^{Me}$CT ATA$^{Me}$CG$^{Me}$CG$^{Me}$CAA TATGG (SEQ ID NO: 3) |
| B | 5-10-5 gapmer The central block of a gapmer is 10 deoxy ribonucleotides, which is flanked by blocks of 2'-OMe ribonucleotides. | $^{Me}$CGA$^{Me}$CU ATA$^{Me}$CG$^{Me}$CG$^{Me}$CAA UAUGG (SEQ ID NO: 4) |
| C | 5-10-5 gapmer The central block of a gapmer is 10 deoxy ribonucleotides, which is flanked by blocks of 2'-MoE ribonucleotides. | $^{Me}$CGA$^{Me}$CT ATA$^{Me}$CG$^{Me}$CG$^{Me}$CAA TATGG (SEQ ID NO: 5) |
| D | 5-10-5 gapmer The central block of a gapmer is 10 deoxy ribonucleotides, which is flanked by blocks of cEt ribonucleotides. | $^{Me}$CGA$^{Me}$CU ATA$^{Me}$CG$^{Me}$CG$^{Me}$CAA UAUGG (SEQ ID NO: 6) |
| E | 5-10-5 gapmer The central block of a gapmer is 10 deoxy ribonucleotides, which is flanked by blocks of 2'-Fluoro ribonucleotides. | CGACU ATA$^{Me}$CG$^{Me}$CG$^{Me}$CAA UAUGG (SEQ ID NO: 7) |

2. BIIB 067 (SEQ ID NO: 2), a 5-10-5 gapmer phosphothioester and phosphodiester mixed backbone oligonucleotide. The central block of a gapmer is 10 deoxy ribonucleotides, which is flanked by blocks of 2'-MoE ribonucleotides.
3. Phosphorothioate oligonucleotides A, B, C, D, and E as shown in Table 2, below.
4. BIIB 078 (SEQ ID NO:8), a 4-8-6 gapmer phosphothioester and phosphodiester mixed backbone oligonucleotide. The central block of a gapmer is 8 deoxy ribonucleotides, which is flanked by blocks of 2'-MoE ribonucleotides.

(SEQ ID NO: 8)

Results

1. BIIB058

BIIB058 was prepared using the process of the invention (i.e., the 3-reactions-cycle) and compared to the conventional 4-reactions per cycle process. PADS and Xanthane Hydride were used as the sulfurization agent. The sulfurization reaction was in recirculation mode for 5 min. The results of each process are shown in Table 3.

TABLE 3

| | BIIB058 crude yield and purity comparison | | |
|---|---|---|---|
| | PADS | | Xanthane Hydride |
| | 4-reactions-cycle | 3-reactions-cycle | 3-reactions-cycle |
| Total oligo Yield (%) | 84.06 | 86.56 | 86.31 |
| DMT-on oligo Yield (%) | 70.81 | 77.12 | 76.89 |

TABLE 3-continued

BIIB058 crude yield and purity comparison

|  | PADS | | Xanthane Hydride |
| --- | --- | --- | --- |
|  | 4-reactions-cycle | 3-reactions-cycle | 3-reactions-cycle |
| Total Purity (%) | 83.08 | 89.19 | 89.09 |
| MS Purity (%) | 91.97 | 93.29 | 93.67 |
| UV Purity (%) | 91.59 | 95.50 | 95.02 |

Figure 3:
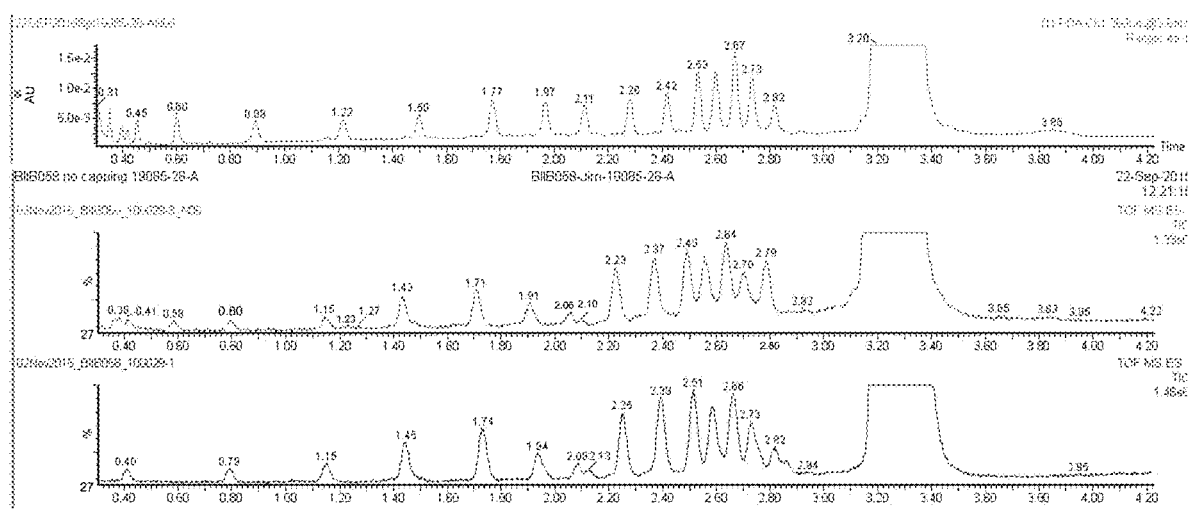
FIG. 3 is a chromatogram comparing the purity by mass spectrometry for the 4-reactions-cycle with PADS (top); 3-reactions-cycle with PADS (middle); and 3-reactions-cycle with xanthane hydride (bottom).
Figure 4:
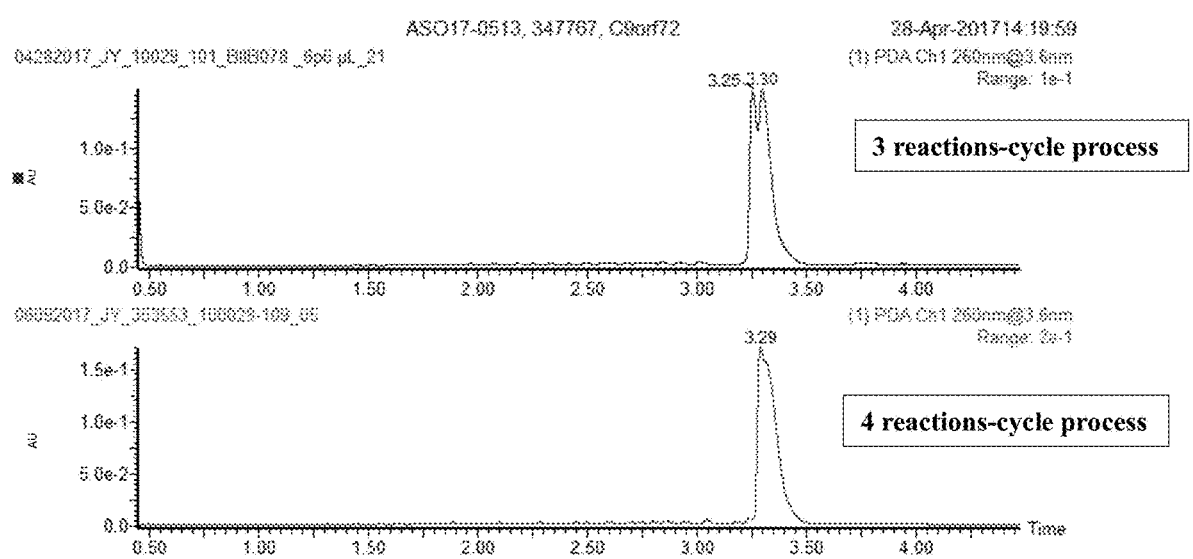
FIGS. 4 and 5 are RPIP HPLC chromatograms comparing the BIIB078 prepared by the 4-reactions-cycle process (bottom) and the 3-reactions-cycle process (top) with PADS as the sulfurization agent.
Figure 5:
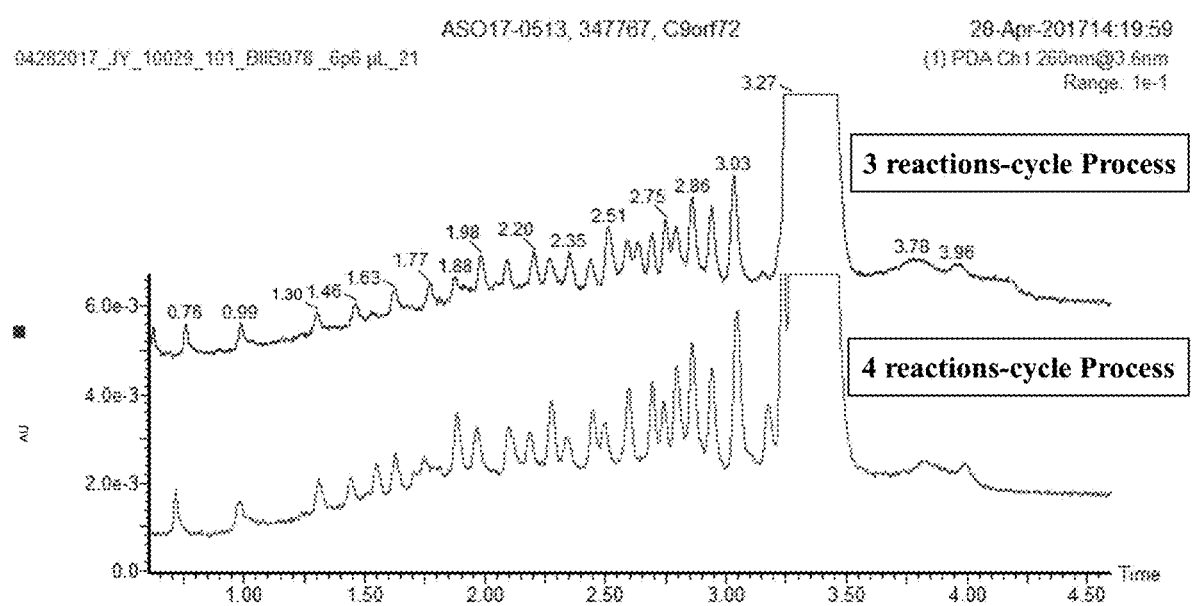
Figure 6:
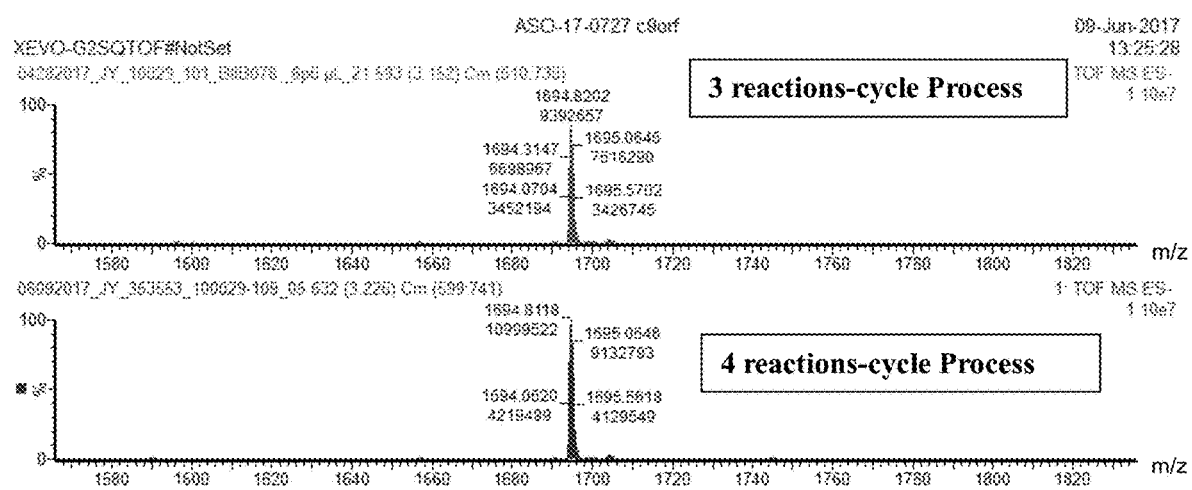
FIGS. 6 and 7 are mass spectrometry chromatograms comparing BIIB078 prepared by the 4-reactions-cycle process (bottom) and the 3-reactions-cycle process (top) with PADS as the sulfurization agent.
Figure 7:
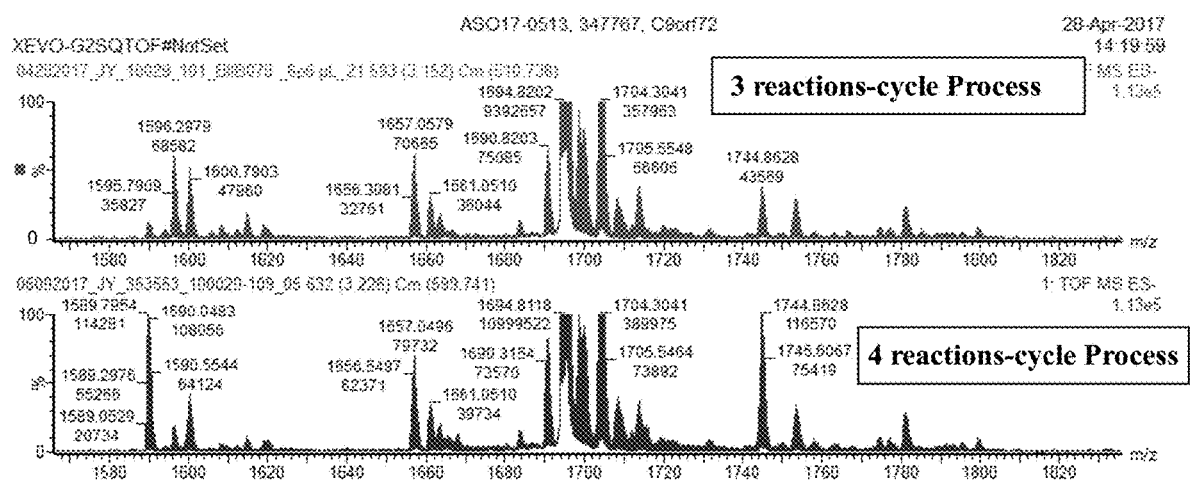

Comparing the 4-reactions-cycle to the 3-reactions-cycle with PADS as the sulfurization agent, the yield and purity of BIIB058 was increased in the 3-reactions-cycle, and no new impurities were generated. Xanthane hydride in the 3-reactions-cycle performed similarly as PADS. A comparison of the mass spectrometry chromatograms is provided in FIG. 3.

2. BIIB067

BIIB067 was prepared using the process of the invention (i.e., the 3-reactions-cycle) and compared to the conventional 4-reactions per cycle process, with PADS used as sulfurization agent. The sulfurization reaction was in recirculation mode for 5 min. Unlike BIIB0058, BIIB067 includes P=O bonds as well as P=S bonds. Therefore, three different reactions were run: 1) the 4 reactions-cycle, 2) the 3 reactions-cycle, and 3) the 3 reactions-cycle with a capping step added only after the oxidation step. Therefore, run 2) would include an oxidation rather than a sulfurization step for that nucleotide, no capping step was done following the oxidation step. The results of each process are shown in Table 4.

TABLE 4

BIIB 067 Crude Yield and Purity Comparison

|  |  | 3 reactions-cycle | |
| --- | --- | --- | --- |
|  | 4 reactions-cycle | Without Capping Reaction after Oxidation | With Capping Reaction after Oxidation |
| Total Oligonucleotide Yield (%) | 86.60 | 95.5 | 101.28 |
| DMT-ON Oligonucleotide (%) | 66.70 | 76.5 | 80.74 |
| Mass purity (%) | 89.00 | 90.70 | 87.84 |
| UV Purity (%) | 86.50 | 88.30 | 90.75 |
| Total Purity (%) | 76.99 | 80.09 | 79.71 |

Comparing the 4-reactions-cycle to the 3-reactions-cycle without a capping reaction after oxidation, the yield and purity of BIIB067 increased, and no new impurities were generated. Inclusion of the capping step following the oxidation reaction only did not improve the overall purity of BIIB067 as prepared by the 3-reactions-cycle. Therefore, the 3-reactions-cycle without capping can be used even with oligonucleotides including P=O bonds.

3. Oligonucleotides A, B, C, D, and E

Oligonucleotides A, B, C, D, and E were prepared using the process of the invention and compared to the conventional 4-reactions per cycle process. Table 5 provides the amidites used for the synthesis. The sulfurization agents used are shown in Table 6.

TABLE 5

Amidites for the synthesis

| 5'ODMT-deoxy-phosphoramidite | H |
| --- | --- |
| 5'ODMT-5'OMe-phosphoramidite | OMe |
| 5'ODMT-2'MoE-phosphoramidite | MoE |
| 5'ODMT-cEt-phosphoramidite | cEt |
| 5'ODMT-2'F-phosphoramidite | F |

TABLE 6

Sulfurization Reagents used for the synthesis of the corresponding oligonucleotides

| Oligonucleotides | Sulfurization Reagent | |
|---|---|---|
| A | XH | PADS |
| B | XH | PADS |
| C | XH | PADS |
| D | XH | PADS |
| E | XH | PADS |

As shown in Table 7, the yield, UV purity, and MS impurity profile of crude oligonucleotide from the process of the invention is similar to the crude oligonucleotide as prepared by the conventional 4-reactions-cycle process.

TABLE 7

Optical yield (OD) and RPIP HPLC purity of DMT-on products

| Sulfurization Reagent | Oligonucleotide | 4 reactions-cycle | 3 reactions-cycle | Conclusion |
|---|---|---|---|---|
| Xanthane Hydride | A | 142.1 OD/μmol UV: 73.61% | 146.8 OD/μmol UV: 78.65% | 1. Yield and UV purity of crude from 3-Reactions-cycle process is similar as crude from 4-Reactions-cycle process. 2. MS impurity profile from 3-Reactions-cycle process is compatible as the crude from 4-Reactions-cycle process. |
| | B | 149.8 OD/μmol UV: 78.20% | 155.7 OD/μmol UV: 79.71% | Same as above |
| | C | 150.4 OD/μmol UV: 80.56% | 154.3 OD/μmol UV: 82.36% | Same as above |
| | D | 126.3 OD/μmol UV: 71.15% | 129.4 OD/μmol UV: 73.31% | Same as above |
| | E | 133.1 OD/μmol UV: 71.34% | 137.8 OD/μmol UV: 73.10% | Same as above |
| PADS | A | 146.7 OD/μmol UV: 83.32% | 154.9 OD/μmol UV: 77.66% | Same as above |
| | B | 150.1 OD/μmol UV: 81.33% | 154.3 OD/μmol UV: 79.17% | Same as above |
| | C | 158.8 OD/μmol UV: 79.27% | 159.2 OD/μmol UV: 78.80% | Same as above |
| | D | 107.5 OD/μmol UV: 72.29% | 129.3 OD/μmol UV: 71.13% | 1. Yield and UV purity of crude from 3-Reactions-cycle process is similar as crude from 4-Reactions-cycle process. 2. MS impurity profile from 3-reactions-cycle process is compatible as the crude from 4-reactions-cycle process. N-1 impurity for 3-reactions-cycle process is higher than the crude from 4-reactions-cycle process. |
| | E | 141.0 OD/μmol UV: 73.90% | 140.9 OD/μmol UV: 75.77% | 1. Yield and UV purity of crude from 3-Reactions-cycle process is similar as crude from 4-Reactions-cycle process. 2. MS impurity profile from 3-Reactions-cycle process is |

TABLE 7-continued

Optical yield (OD) and RPIP HPLC purity of DMT-on products

| Sulfurization Reagent | Oligonucleotide | 4 reactions-cycle | 3 reactions-cycle | Conclusion |
|---|---|---|---|---|
| | | | | compatible as the crude from 4-Reactions-cycle process. |
| Beaucage Reagent | A | 167.4 OD/μmol UV: 79.70% | 166.1 OD/μmol UV: 78.39% | Same as above |

4. BIIB 078

BIIB078 was prepared using the process of the invention (i.e., the 3-reactions-cycle) and compared to the conventional 4-reactions per cycle process. PADS was used as the sulfurization agent. The sulfurization reaction was in recirculation mode for 3 min. The results of each process are shown in Table 8 and FIGS. 4-7.

TABLE 8

BIIB 078 crude yield and purity comparison

| | PADS | |
|---|---|---|
| | 4 reactions-cycle Process | 3 reactions-cycle Process |
| DMT-on oligo Yield (%) | 63.5 | 71.7 |
| Total Purity (%) | 81.29 | 83.46 |
| MS Purity (%) | 86.80 | 87.82 |
| UV Purity (%) | 93.65 | 95.04 |

Comparing the 4-reactions-cycle to the 3-reactions-cycle with PADS as the sulfurization agent, the yield and purity of BIIB078 was increased in the 3-reactions-cycle, and no new impurities were generated. Comparisons of HPLC chromatograms and mass spectrometry chromatograms and are provided in FIGS. 4-7.

Example 2. NMR Study of the Dual Roles of PADS for the Sulfurization and Capping In the first NMR experiment, PADS was aged in 3-picoline in acetonitrile-d3 at 22° C. for 16 h (Scheme 1). After the aging, n-BuOH was added in the solution and NMR spectra were taken at different time points. The spectra showed that the formation of $PhCH_2CO_2Bu$ was very slow.

Figure 8:
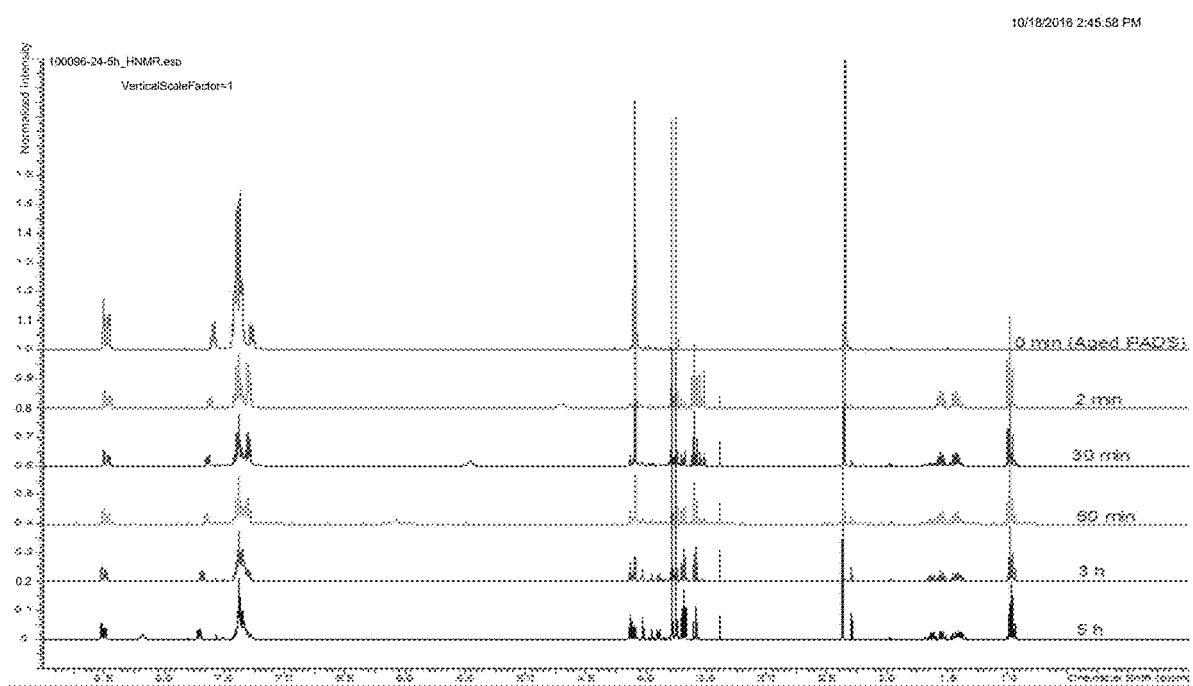
FIG. 8 shows $^1$H NMR spectra for reaction mixture of BuOH, P(OMe)$_3$ and PADS over time, wherein PADS was aged with 3-picoline in acetonitrile-d3.

In a separate experiment following the same procedure as above, after addition of BuOH, to the reaction mixture was added $P(OMe)_3$ and the NMR spectra of the reaction mixture were recorded at different time points. $P(OMe)_3$ has a similar structure as the phosphite intermediates in the solid phase synthesis. The spectra showed that in about 2 min sulfurization of $P(OMe)_3$ completed and esterification (capping) of BuOH occurred (FIG. 8).

These experimental results demonstrated that during the sulfurization an active capping reagent was generated and it capped the alcohol present.

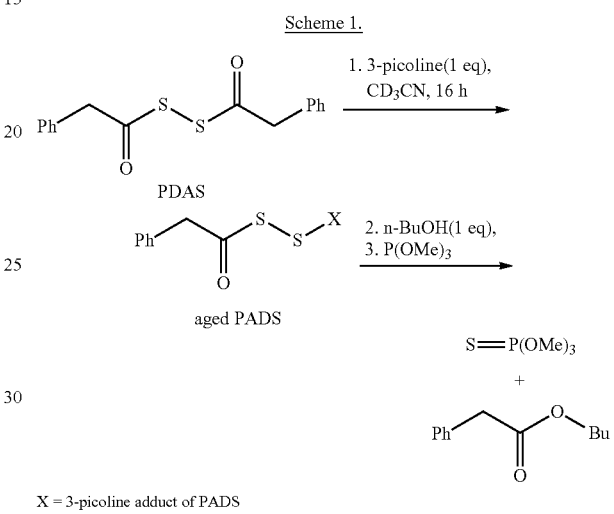

Scheme 1.

X = 3-picoline adduct of PADS

Figure 9:
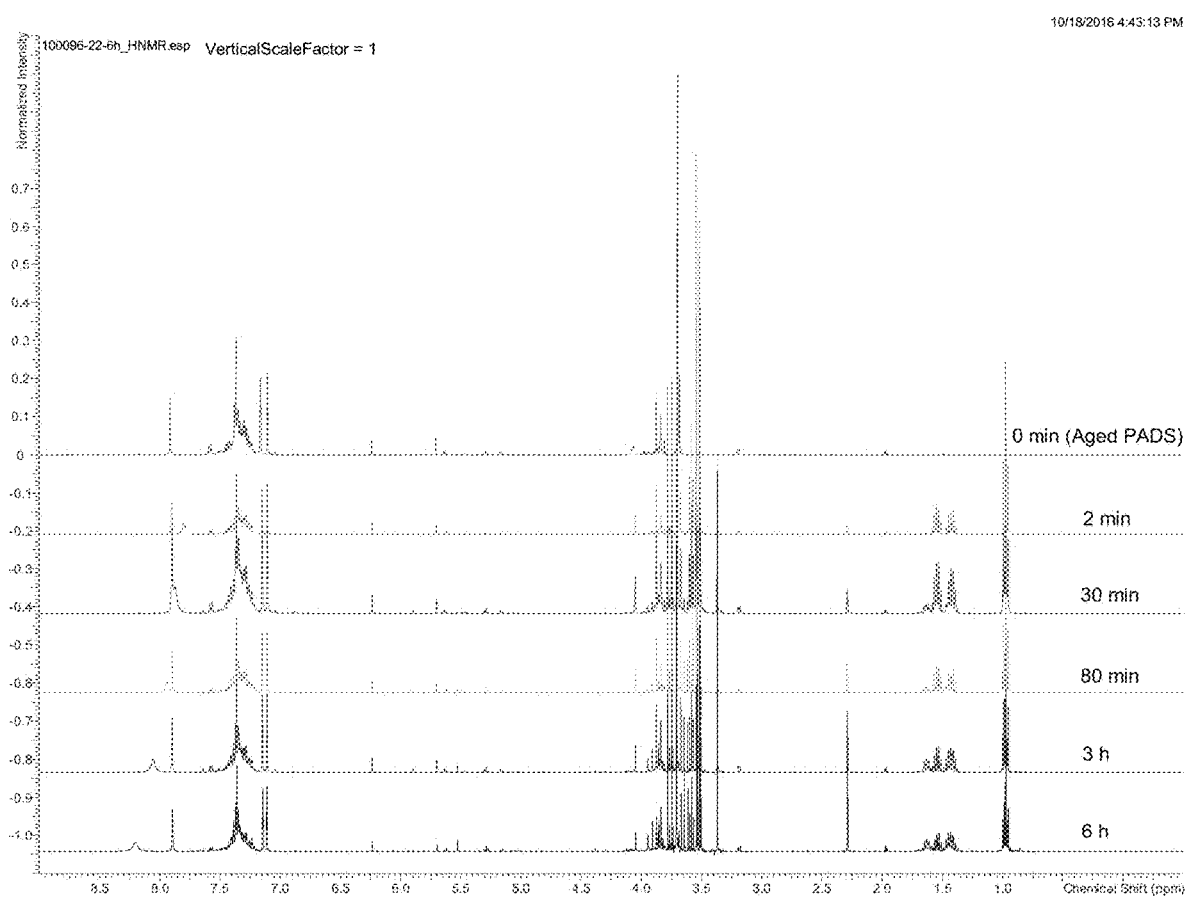
FIG. 9 shows ¹H NMR spectra for reaction mixture of BuOH, P(OMe)₃ and PADS over time, wherein PADS was aged with N-methyl imidazole in acetonitrile-d3.

The same experiments were repeated with N-methyl imidazole as the base to age the PADS and similar results were obtained (Scheme 2). Without adding $P(OMe)_3$, the esterification reaction was very slow, but esterification of BuOH occurred immediately after the sulfurization reaction. These results again showed that the sulfurization and capping occurred once sulfurization happened (FIG. 9).

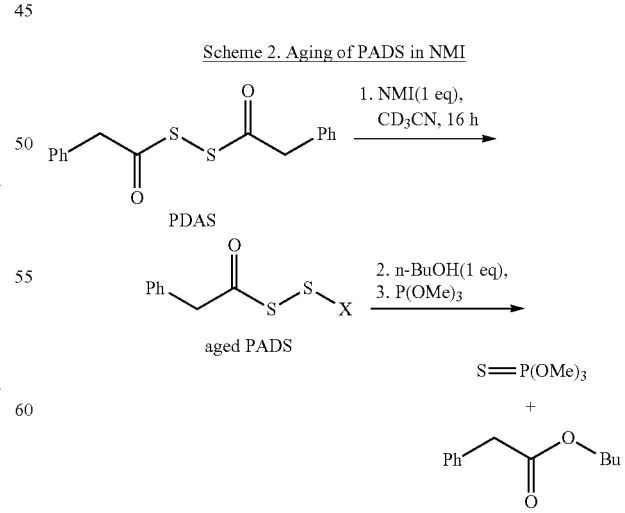

Scheme 2. Aging of PADS in NMI

NMI: N-methyl imidazole
X = NMI adduct of PADS

What is claimed is:

1. A process for preparing an oligonucleotide comprising
a) reacting the compound of Formula (I):

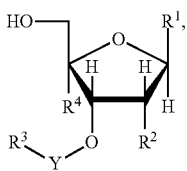

with the compound of Formula (II):

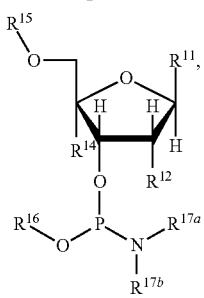

to form a compound of Formula (III):

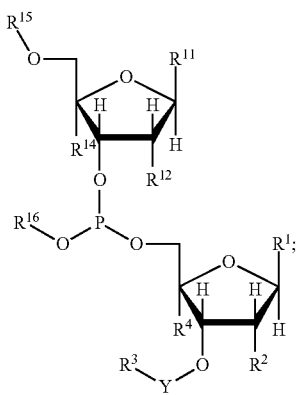

and
b) sulfurizing the compound of Formula (III) with a sulfurization agent to form a compound of Formula (IV):

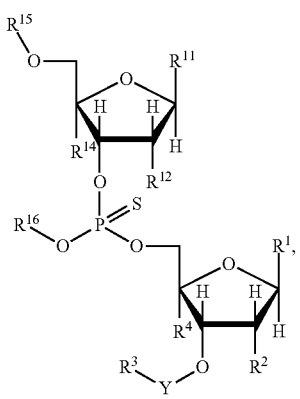

and from unreacted compound of Formula (I) forms a compound of Formula (V):

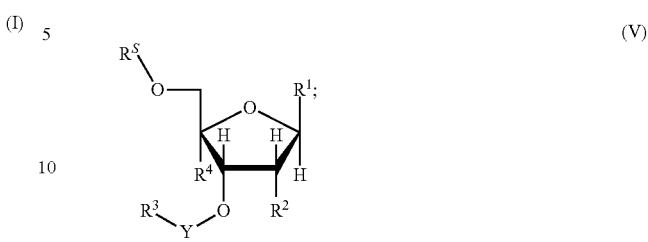

wherein
each $R^1$ and $R^{11}$ are independently a nucleobase, wherein the $NH_2$ of the nucleobase, if present, is protected by an amine protecting group;
each $R^2$ and $R^{12}$ are independently selected from the group consisting of H, halo, and $C_{1-6}$alkoxy optionally substituted with $C_{1-6}$alkoxy;
$R^3$ is a solid support;
Y is absent, a nucleotide, or an oligonucleotide comprising 2 to 50 nucleotides;
each $R^4$ is H;
each $R^{14}$ is H;
$R^{15}$ is a hydroxy protecting group;
$R^{16}$ is $CH_2CH_2CN$;
$R^{17a}$ and $R^{17b}$ are independently $C_{1-6}$alkyl;
wherein the sulfurization agent is (i) 3-amino-1,2,4-dithiazole-5-thione (XH or ADTT); (ii) phenylacetyl disulfide (PADS); (iii) 3-(dimethylamino-methylidene) amino)-3H-1,2,4-dithiazole (DDTT); or (iv) 3H-1,2-benzodithiol-3-one 1,1-dioxide;
wherein $R^S$ is —C(SH)(=N)—CN; —C(=O)CH_2C_6H_5; —C(=S)NHC(=S)N=CHN(CH_3)_2; or

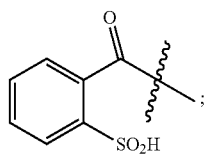

wherein the sulfurization agent is reacted for a sufficient amount of time to substantially completely convert unreacted compound of Formula (I) to the compound of Formula (V) and to convert the compound of Formula (III) to Formula (IV);
wherein a sufficient amount of sulfurization agent is added to substantially completely convert unreacted compound of Formula (I) to Formula (V) and to convert the compound of Formula (III) to Formula (IV); and
wherein the compounds of Formulas (I), (II), (III), (IV), and (V) are optionally in the form of a pharmaceutically acceptable salt;
provided that sulfurization step (b) is not followed by a capping step.

2. The process of claim 1, further comprising the step of c) deprotecting the compound of Formula (IV) to form the compound of Formula (VI):

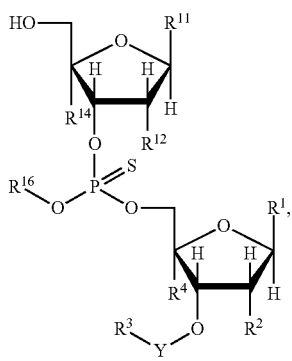

(VI)

or a pharmaceutically acceptable salt thereof.

3. The compound of claim 2, further comprising the step of d) reacting the compound of Formula (VI) with a compound of Formula (II) to form a compound of Formula (VII):

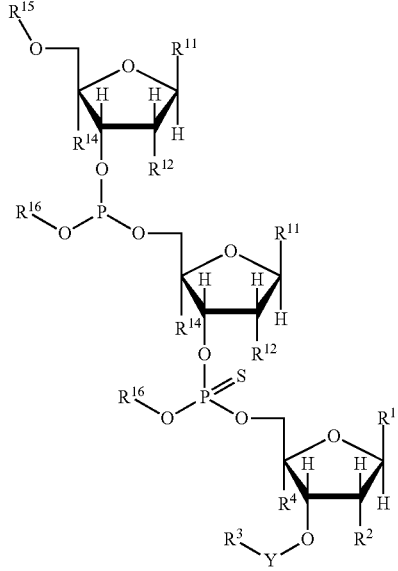

(VII)

or a pharmaceutically acceptable salt thereof; and e) oxidizing the compound of Formula (VII) with an oxidizing agent to form a compound of Formula (VIII):

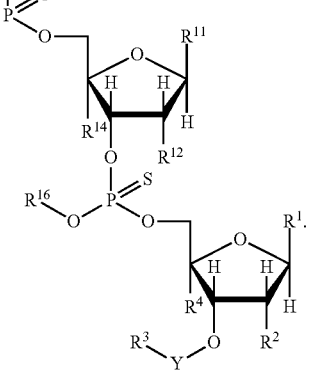

(VIII)

4. The process of claim 3, further comprising the step of f) deprotecting the compound of Formula (VIII) to form the compound of Formula (IX):

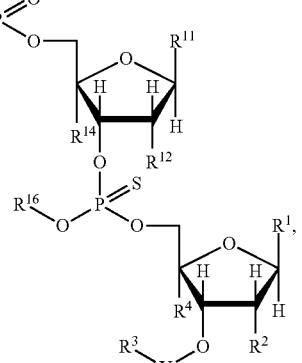

(IX)

or a pharmaceutically acceptable salt thereof.

5. The process of claim 4, wherein starting with the compound of Formula (VI) or the compound of Formula (IX), steps a), b), and c) are repeated n times and steps d), e), and f) are repeated m times, wherein repetition of steps a), b), and c) and steps d), e) and f) can occur in any order relative to each other, wherein n is at least 1 and m is 0, 1, 2, 3, or 4, to form an oligonucleotide of Formula (X) or (XI):

agent or the byproduct of the sulfurization agent following the sulfurization step to form a compound of Formula (XII) or (XIII):

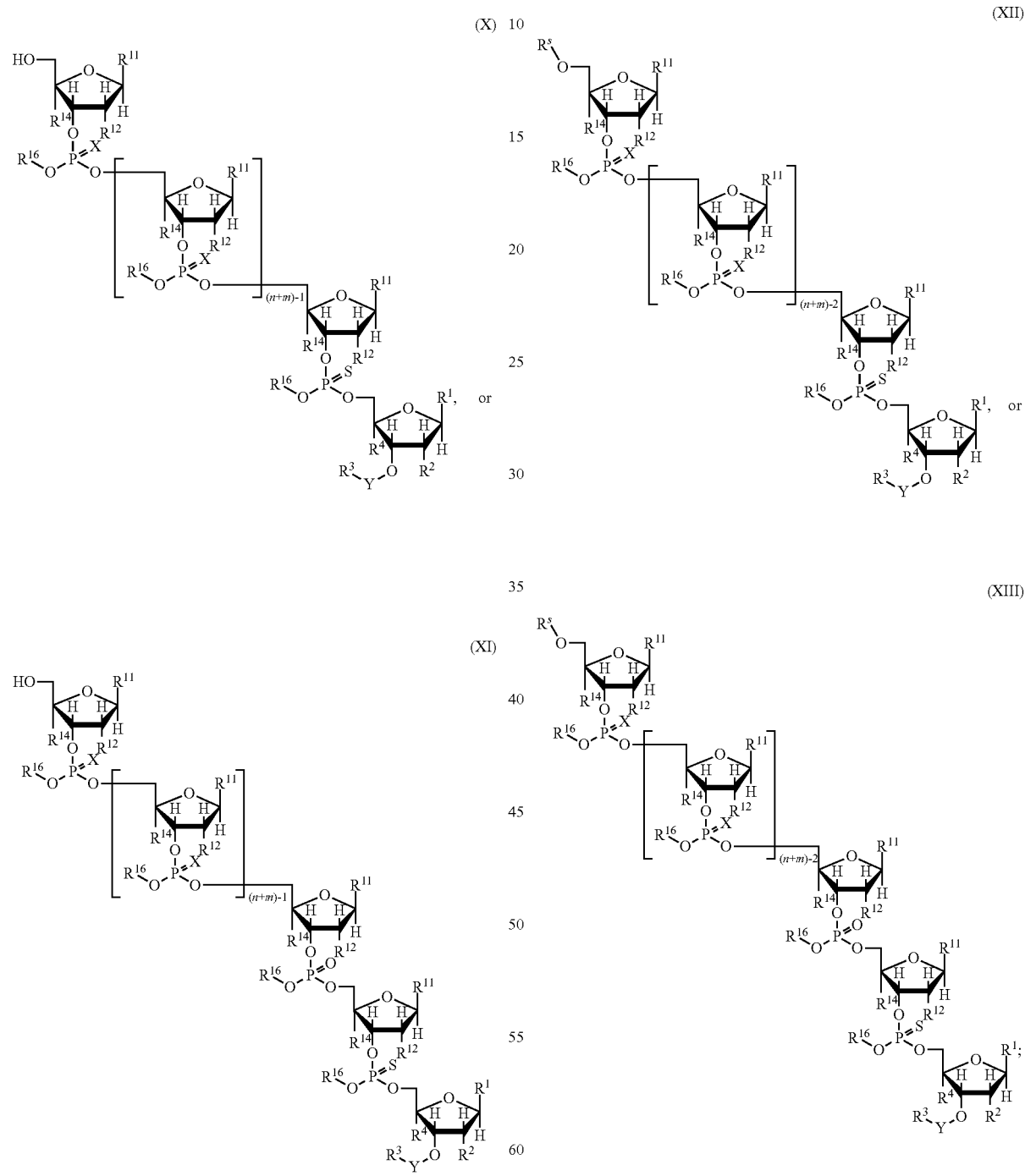

or a pharmaceutically acceptable salt thereof, or forms a oligonucleotide wherein each repetition of steps a, b, and c, or steps d, e, and f results in some unreacted compound of Formula (VI) or (IX) that reacts with excess sulfurization wherein each X is independently selected from S or O, provided that X is O only 4, 3, 2, 1, or 0 times in the compound of Formula (X), (XI), (XII), or (XIII).

6. The process of claim 4, further comprising the step of g) reacting the unreacted compound of Formula (VI) with a capping agent to form the compound of Formula (XIV):

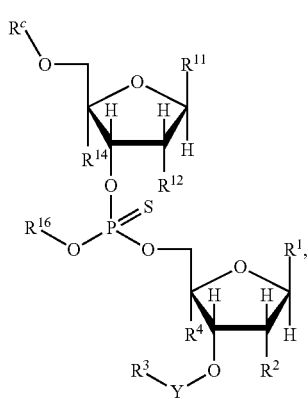

(XIV)

or a pharmaceutically acceptable salt thereof,
wherein $R^c$ is a hydroxy protecting group formed from the capping agent, wherein the capping agent is acetic anhydride and $R^c$ is acetyl.

7. The process of claim 6, further comprising the step of h) deprotecting the compound of Formula (VIII) to form the compound of Formula (IX):

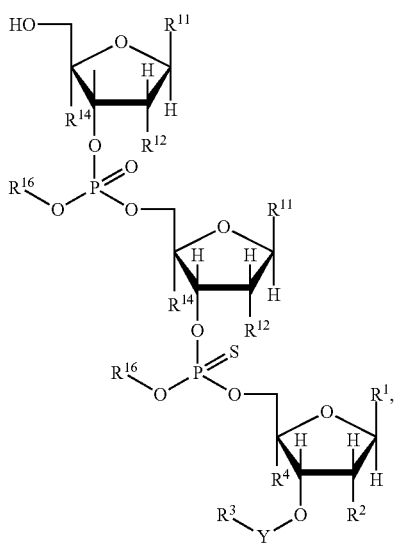

(IX)

or a pharmaceutically acceptable salt thereof.

8. The process of claim 7, wherein starting with the compound of Formula (VI) or the compound of Formula (IX),

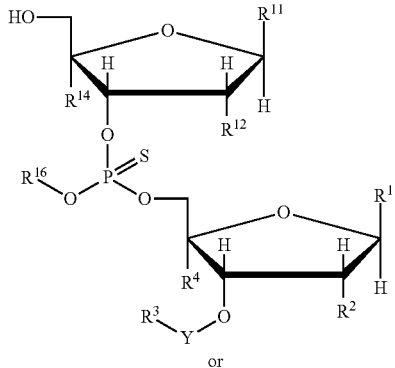

(VI)

or

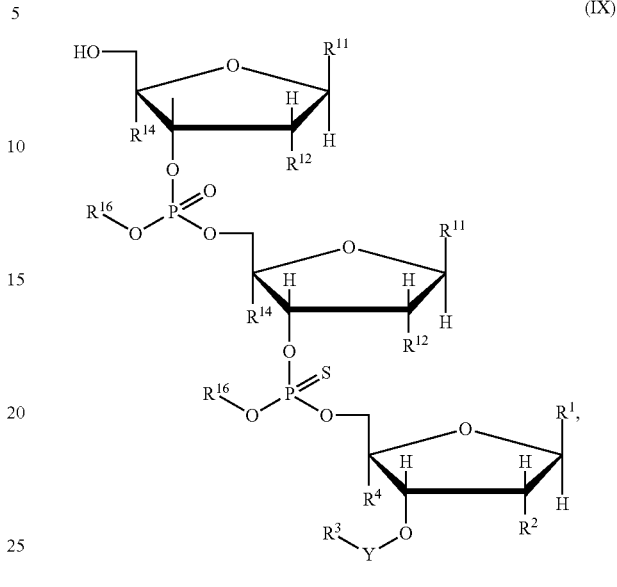

(IX)

steps a), b), and c) are repeated n times and steps d), e), g) and h) are repeated m times, wherein repetition of steps a), b), and c) and steps d), e), g) and h) can occur in any order relative to each other, wherein n is at least 1 and m is 0 to 10 form an oligonucleotide of Formula (X) or (XVII):

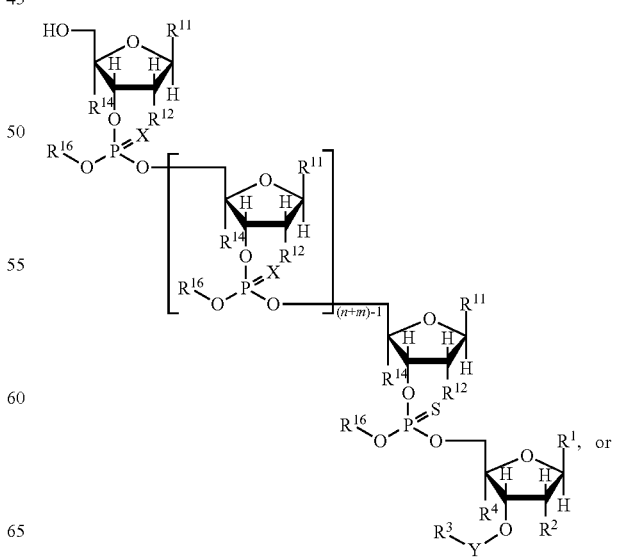

(X)

(XI)

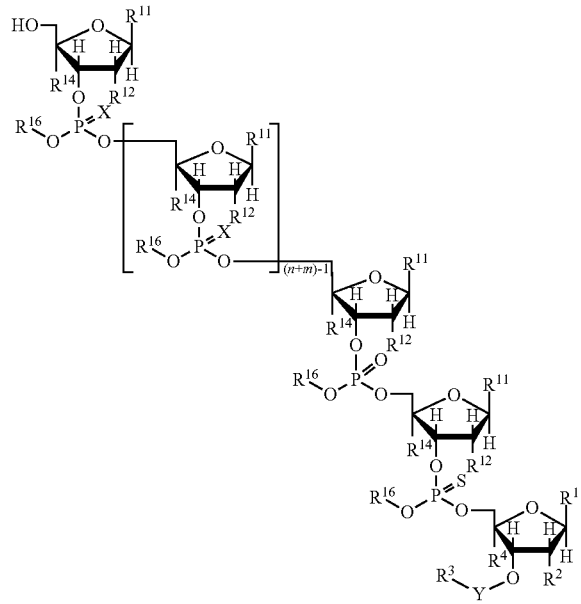

or a pharmaceutically acceptable salt thereof, or forms a oligonucleotide wherein each repetition of steps a, b, and c, or steps d, e, and f results in some unreacted compound of Formula (VI) or (IX) that reacts with excess sulfurization agent or the byproduct of the sulfurization agent following the sulfurization step to form a compound of Formula (XII) or (XIII):

(XII)

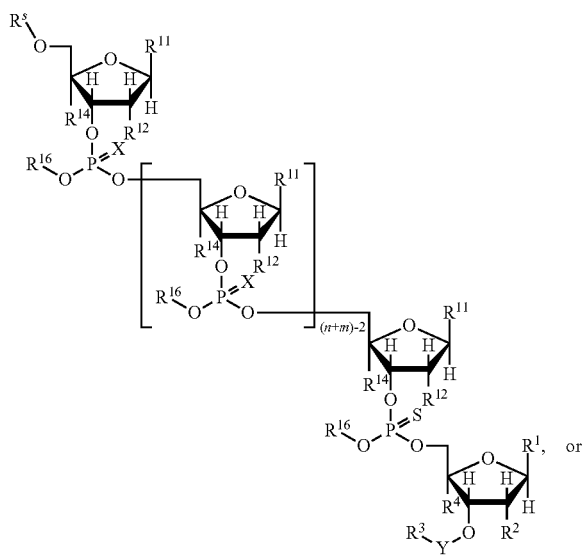

or (XIII)

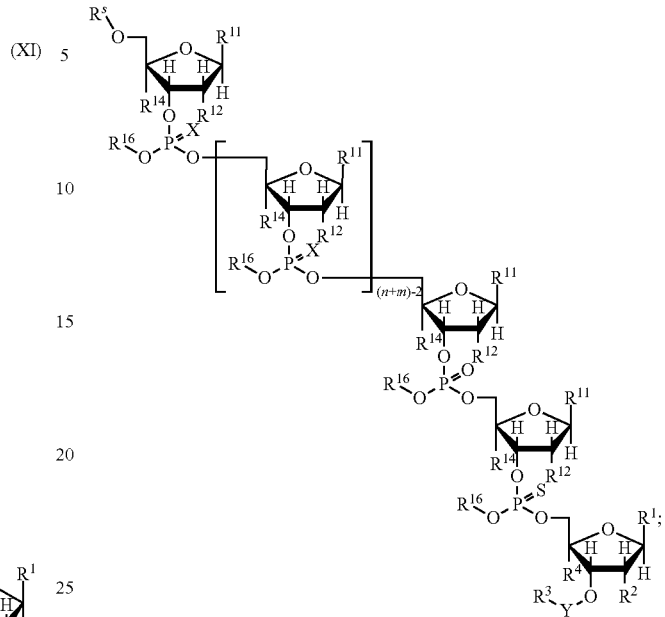

wherein each X is independently selected from S or O.

9. The process of claim 8, wherein n is 2 to 1000, 2 to 500, 2 to 50, or 2 to 25.

10. The process of claim 5, wherein compound of Formula (X) is an anti-sense oligonucleotide comprising 2 to 30 nucleotides.

11. The process of claim 10, wherein the anti-sense oligonucleotide comprises (i) modified RNA only; (ii) DNA and modified RNA; or (iii) DNA only.

12. The process of claim 10, wherein the sequence of the anti-sense oligonucleotide is SEQ ID NO: 1, SEQ ID NO: 2 or SEQ ID NO: 8.

13. The process of claim 1, wherein the sulfurization agent is phenylacetyl disulfide (PADS) and $R^S$ is —C(=O)CH$_2$C$_6$H$_5$.

14. The process of claim 1, wherein the sulfurization agent is recirculated across the solid support 1-20 times, 1-10 times, or 1-5 times.

15. The process of claim 1, wherein the sulfurization agent is reacted by recirculating across the solid support 3 to 6 equivalents of sulfurization agent relative to the linker or the first nucleotide if the first nucleotide is directly attached to the solid support.

16. The process of claim 1, wherein the sulfurization reagent is 3-(dimethylamino-methylidene)amino)-3H-1,2,4-dithiazole (DDTT) added at a concentration of 0.02 M to 0.1 M.

17. The process of claim 1, wherein the nucleobase is selected from the group consisting of 1-cytosinyl, 9-guaninyl, 9-adeninyl, 1-thyminyl, 1-uracilyl, 9-hypoxanthinyl, 9-xanthinyl, 7-methyl-9-guaninyl, 5,6-dihydrouracilyl, 5-methyl-1-cytosinyl, and 5-hydroxymethyl-1-cytosinyl, wherein the NH$_2$ group of the nucleobase, if present, is protected by PhCO—, CH$_3$CO—, iPrCO—, Me$_2$N—CH=, or Me$_2$N—CMe=.

18. The process of claim 1, wherein
each $R^2$ and $R^{12}$ are independently selected from the group consisting of H, F, and C$_{1-4}$alkoxy optionally substituted with C$_{1-4}$alkoxy;

each $R^4$ is independently H or forms a ring with the alkoxy group of $R^2$, wherein the ring is a 5 or 6-membered ring optionally substituted with 1 to 3 $C_{1-4}$ alkyl groups;

$R^{16}$ is —$CH_2CH_2CN$;

$R^{17a}$ and $R^{17b}$ are independently $C_{1-4}$alkyl; and each $R^{14}$ is independently H or forms a ring with the alkoxy group of $R^{12}$, wherein the ring is a 5 or 6-membered ring optionally substituted with 1 to 3 $C_{1-4}$ alkyl groups.

19. The process of claim 1, wherein each $R^2$ and $R^{12}$ are independently selected from H or $C_{1-4}$alkoxy optionally substituted with $C_{1-4}$alkoxy;

$R^{15}$ is 4,4'-dimethoxytrityl;

$R^{16}$ is —$CH_2CH_2CN$;

$R^{17a}$ and $R^{17b}$ are independently $C_{1-6}$alkyl; and $R^S$ is —$C(=N)(SH)$—$CN$ or —$C(=O)CH_2C_6H_5$.

20. The process of claim 1, wherein Y is absent, a single nucleotide or an oligonucleotide comprising 2 to 40, 2 to 30 or 2 to 25 nucleotides.

21. The process of claim 1, wherein the solid support is an unylinker solid support.

\* \* \* \* \*